(12) United States Patent
Bainbridge et al.

(10) Patent No.: US 6,899,691 B2
(45) Date of Patent: May 31, 2005

(54) EXTRACORPOREAL BLOOD PROCESSING METHODS AND APPARATUS

(75) Inventors: Marlene A. Bainbridge, Lakewood, CO (US); Thomas J. Felt, Boulder, CO (US)

(73) Assignee: Gambro Inc., Lakewood, CO (US)

( * ) Notice: Subject to any disclaimer, the term of this patent is extended or adjusted under 35 U.S.C. 154(b) by 394 days.

(21) Appl. No.: 09/746,987

(22) Filed: Dec. 22, 2000

(65) Prior Publication Data

US 2001/0048892 A1 Dec. 6, 2001

Related U.S. Application Data

(60) Provisional application No. 60/171,932, filed on Dec. 22, 1999.

(51) Int. Cl.$^7$ ............................................. A61M 37/00
(52) U.S. Cl. ...................... 604/4.01; 604/6.01; 604/67; 210/741; 210/90
(58) Field of Search ............................. 604/4.01, 5.01, 604/5.02, 6.01, 6.11, 6.1, 6.04, 7, 65, 67; 210/741, 787, 767, 90, 97, 103, 96.2, 138, 87, 85; 417/44.4, 44.2

(56) References Cited

U.S. PATENT DOCUMENTS

| | | | |
|---|---|---|---|
| 3,655,123 A | | 4/1972 | Judson et al. |
| 3,709,222 A | | 1/1973 | DeVries |
| 3,946,731 A | * | 3/1976 | Lichtenstein ............ 128/214 R |
| 4,024,483 A | | 5/1977 | Tomczak et al. |
| 4,080,966 A | | 3/1978 | McNally et al. |
| 4,086,924 A | | 5/1978 | Latham, Jr. |
| 4,146,172 A | | 3/1979 | Cullis et al. |
| 4,148,314 A | | 4/1979 | Yin ............................. 128/214 |
| 4,174,637 A | | 11/1979 | Mulzet et al. |
| 4,185,629 A | * | 1/1980 | Cullis et al. ............ 128/214 R |
| 4,227,420 A | | 10/1980 | Lamadrid |

(Continued)

FOREIGN PATENT DOCUMENTS

| | | |
|---|---|---|
| EP | 0834329 | 4/1998 |
| WO | WO 00/12991 | 3/2000 |

OTHER PUBLICATIONS

Fresenius Operation Manual, *Fresenius MT AS 104 Blood Cell Separator*, Section 3 Safety and Alarm Circuits; Section 4, Remedies in Case of Alarm or Error Conditions; Section 6, "Definitions and Terms"; Section 7, :Tables and Figures (1990).

(Continued)

*Primary Examiner*—Henry Bennett
*Assistant Examiner*—Camtu Nguyen
(74) *Attorney, Agent, or Firm*—Edna M. O'Connor; Laura M. Butterfield

(57) ABSTRACT

A method and apparatus for controlling a fluid separation system in response to fluid pressure changes in a fluid flow, said method comprising the steps of sensing a fluid pressure; comparing the fluid pressure to a threshold value, and if the fluid pressure is below the threshold value, then pausing fluid flow for a selected period. During the selected period, either the fluid pressure sensed automatically resolves or the method further comprises a step of setting a fall alarm condition. The method and apparatus may further include interpreting a particular quantity of below threshold fluid pressure occurrences where the fluid pressure is below the threshold value occurring within a particular time period, and then, signalling an alarm. Threshold values may be calculated by the method or apparatus according to a formula such as the following:

Threshold Value=Config+75−0.3309*$Q_{in}$/(1−$H_{in}$)−0.3026*$Q_n$/(1−$H_n$);

where,
Config=a configuration pre-selected pressure value;
$Q_{in}$=fluid flow rate in the inlet tubing line;
$H_{in}$=Hematocrit in the inlet tubing line;
$Q_n$=fluid flow rate in the needle; and
$H_n$=Hematocrit in the needle.

33 Claims, 13 Drawing Sheets

U.S. PATENT DOCUMENTS

| | | | |
|---|---|---|---|
| 4,231,366 A | | 11/1980 | Schael |
| 4,263,808 A | | 4/1981 | Bellotti et al. |
| 4,285,464 A | | 8/1981 | Latham, Jr. |
| 4,370,983 A | | 2/1983 | Lichtenstein |
| 4,385,630 A | | 5/1983 | Glicher et al. |
| 4,425,114 A | | 1/1984 | Schoendorfer et al. |
| 4,436,620 A | | 3/1984 | Bellotti et al. |
| 4,468,219 A | | 8/1984 | George et al. |
| 4,479,761 A | | 10/1984 | Bilstad et al. |
| 4,501,531 A | | 2/1985 | Bilstad et al. |
| 4,637,813 A | * | 1/1987 | DeVries .................... 604/6 |
| 4,661,246 A | | 4/1987 | Ash |
| 4,710,164 A | | 12/1987 | Levin et al. |
| 4,718,891 A | | 1/1988 | Lipps |
| 4,739,492 A | | 4/1988 | Cochran |
| 4,798,090 A | | 1/1989 | Heath et al. |
| 4,828,543 A | * | 5/1989 | Weiss et al. .................... 604/4 |
| 4,850,998 A | * | 7/1989 | Schoendorfer ............... 604/28 |
| 4,883,462 A | | 11/1989 | Williamson et al. |
| 4,911,703 A | | 3/1990 | Lysaght et al. |
| 4,923,439 A | * | 5/1990 | Seidel et al. .................... 604/6 |
| 5,069,792 A | | 12/1991 | Prince et al. |
| 5,120,303 A | | 6/1992 | Hombrouckx |
| 5,171,212 A | * | 12/1992 | Buck et al. .................... 604/4 |
| 5,174,894 A | | 12/1992 | Ohsawa et al. |
| 5,178,603 A | * | 1/1993 | Prince .......................... 604/6 |
| 5,186,431 A | * | 2/1993 | Tamari .......................... 251/5 |
| 5,200,090 A | | 4/1993 | Ford et al. |
| 5,370,123 A | | 12/1994 | Shinzato |
| 5,372,709 A | | 12/1994 | Hood |
| 5,431,811 A | | 7/1995 | Tusini et al. |
| 5,437,624 A | | 8/1995 | Langley |
| 5,472,614 A | * | 12/1995 | Rossi .......................... 210/646 |
| 5,487,827 A | | 1/1996 | Peterson et al. |
| 5,499,648 A | * | 3/1996 | Powell et al. ................. 137/15 |
| 5,501,665 A | | 3/1996 | Jhuboo et al. |
| 5,536,237 A | | 7/1996 | Prince et al. |
| 5,555,910 A | * | 9/1996 | Powell et al. ............... 137/488 |
| 5,618,441 A | | 4/1997 | Rosa et al. |
| 5,653,887 A | | 8/1997 | Wahl et al. |
| 5,690,831 A | | 11/1997 | Kenley et al. |
| 5,711,883 A | | 1/1998 | Folden et al. |
| 5,762,805 A | | 6/1998 | Truitt et al. |
| 5,776,345 A | | 7/1998 | Truitt et al. .................. 210/645 |
| 5,795,317 A | | 8/1998 | Brierton et al. ................. 604/5 |
| 5,806,553 A | * | 9/1998 | Sidwell .................... 137/487.5 |
| 5,827,223 A | | 10/1998 | Butterfield |
| 5,837,150 A | * | 11/1998 | Langley et al. ............. 210/782 |
| 5,906,589 A | * | 5/1999 | Gordon et al. ................. 604/65 |
| 5,910,252 A | * | 6/1999 | Truitt et al. .................. 210/645 |
| 5,919,154 A | * | 7/1999 | Toavs et al. .................... 604/4 |
| 5,921,950 A | * | 7/1999 | Toavs et al. .................... 604/4 |
| 5,941,842 A | * | 8/1999 | Steele et al. .................... 604/4 |
| 5,954,971 A | | 9/1999 | Pages et al. |
| 5,992,449 A | * | 11/1999 | Sprague ..................... 137/488 |
| 6,033,561 A | * | 3/2000 | Schoendorfer ........... 210/195.1 |

OTHER PUBLICATIONS

Shoendorfer, D.W. "Automation in Apheresis" pp. 129–146, undated, in use 1 year prior to filing.

Baxter Helathcare Corporation, *CS–300 Plus Parameter Changes, Operator's Manual*, Chapter 1, "Description"; Chapter 4, "Warnings"; Chapter 5, "Precautions"; Chapter 8, "Information for Use"; Chapter 9, "Run Procedures"; Chapter 12, "Troubleshooting", pp. 12–12 through 12–36, undated, in use 1 year prior to filing.

COBE BCT, Inc.*COBE Spectra Apheresis System, Operator's Manual*, "Table of Contents"; Section 1 "Introduction"; Section 4A, "Platelet Dual–Needle Operation"; Section 9, "Diagnostics" (1991).

* cited by examiner

EXTRACORPOREAL BLOOD PROCESSING METHODS AND APPARATUS

This application claims the benefit of U.S. provisional application No. 60/171,932 filed Dec. 22, 1999.

FIELD OF THE INVENTION

The present invention generally relates to the field of extracorporeal blood processing and, more particularly, to methods and apparatus which may be incorporated into an automated apheresis system for blood component collection or therapy.

BACKGROUND OF THE INVENTION

One type of extracorporeal blood processing is an apheresis procedure in which blood is removed from a donor or patient, directed to a blood component separation device (e.g., centrifuge), and separated into various blood component types (e.g., red blood cells, white blood cells, platelets, plasma) for collection or therapeutic purposes. One or more of these blood component types are collected (e.g., for transfusion purposes), while the remainder are returned to the donor or patient.

A number of factors affect the commercial viability of an apheresis system. One factor relates to the operator of the system, specifically the time and/or expertise required of an individual to prepare and operate the apheresis system. For instance, reducing the time required by the operator to load and unload the disposables, as well as the complexity of these actions, can increase productivity and/or reduce the potential for operator error. Moreover, reducing the dependency of the system on the operator may lead to reductions in operator errors and/or to reductions in the credentials desired/required for the operators of these systems.

Donor-related factors may also impact the commercial viability of an apheresis system and include donor convenience and donor comfort. For instance, donors typically have only a certain amount of time which may be committed to visiting a blood component collection facility for a donation. Consequently, once at the collection facility the amount of the donor's time which is actually spent collecting blood components is another factor which should be considered. This also relates to donor comfort in that many view the actual collection procedure as being somewhat discomforting in that at least one and sometimes two access needles are in the donor throughout the procedure.

Performance-related factors continue to affect the commercial viability of an apheresis system as well. Performance may be judged in terms of the "collection efficiency" of the apheresis system, which may in turn reduce the amount of donation time and thus increase donor convenience. The "collection efficiency" of a system may of course be gauged in a variety of ways, such as by the amount of a particular blood component type which is collected in relation to the number of this blood component type which passes through the apheresis system. Performance may also be evaluated based upon the effect which the apheresis procedure has on the various blood component types. For instance, it is desirable to minimize the adverse effects on the blood component types as a result of the apheresis procedure (e.g., limit hemolysis and platelet activation).

A particularly important performance-related factor involves the control of the access or draw pressure of the blood being drawn from the donor or patient. Properly maintained access/draw pressures contribute to the reduction of donation times and the minimization of donor/patient discomfort. Also, certain access/draw pressure conditions signify no flow or improper flow characteristics which should be addressed by an operator. For example, it is well known that the access/draw needle may become improperly seated or blocked within the donor/patient access site. Access/draw pressures sensed by the apheresis system can be interpreted as indicating such a problem and then activating an alarm for operator intervention and/or pump controls such as pump slowing or stoppage.

SUMMARY OF THE INVENTION

The present invention generally relates to extracorporeal blood processing. Since each of the various aspects of the present invention may be incorporated into an apheresis system (e.g., whether for blood component collection in which "healthy" cells or other components are removed from the blood or for therapeutic purposes in which "unhealthy" cells or other components are removed from the blood), the present invention will be described in relation to this particular application. However, at least certain of the aspects of the present invention may be suited for other extracorporeal blood processing applications and such are within the scope of the present invention.

An apheresis system which may embody one or more aspects of the present invention generally includes a blood component separation device (e.g., a membrane-based separation device, or a rotatable centrifuge element, such as a rotor, which provides the forces required to separate blood into its various blood component types (e.g., red blood cells, white blood cells, platelets, and plasma)). In one embodiment, the separation device includes a channel which receives a blood processing vessel. Typically, a healthy human donor or a patient suffering from some type of illness (hereafter, both collectively referred to as a donor/patient) is fluidly interconnected with the blood processing vessel by an extracorporeal tubing circuit, and preferably the blood processing vessel and extracorporeal tubing circuit collectively define a closed, sterile system. When the fluid interconnection is established, blood may be extracted from the donor/patient and directed to the blood component separation device such that at least one type of blood component may be separated and removed from the blood, either for collection or for therapy.

One aspect of the present invention relates to improved automated pressure monitoring and alarm handling in extracorporeal blood processing applications.

Another aspect is improving the automated responses of an extracorporeal blood processing device to certain pressure conditions.

These and other features of the present invention will be further illuminated in the following detailed description read in conjunction with the accompanying drawings which are described briefly below.

DETAILED DESCRIPTION

The present invention will be described in relation to the accompanying drawings which assist in illustrating the pertinent features thereof. Generally, the present invention relates to improvements in a blood apheresis system. However, certain of these improvements may be applicable to other extracorporeal blood processing applications and such are within the scope of the present invention as well.

Figure 1:
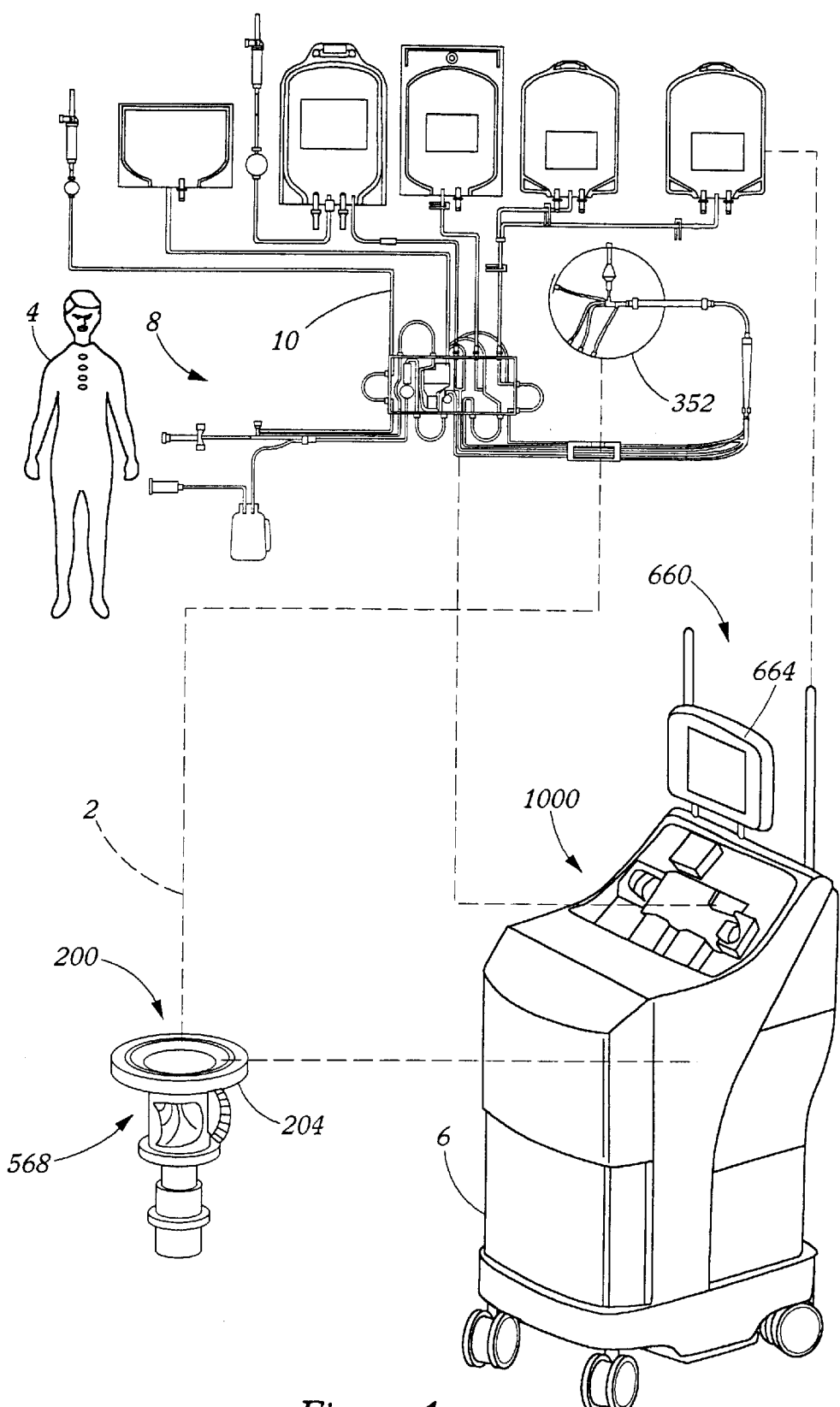
FIG. 1 is a schematic view of one embodiment of an extracorporeal system.

A blood apheresis system 2 such as is schematically illustrated in FIG. 1 allows for a continuous blood component separation process. Generally, whole blood is withdrawn from a donor/patient 4 and is provided to a blood component separation device 6 where the blood is separated into the various component types and at least one of these blood component types is removed from the device 6. These separated blood components may then be collected for subsequent use by transfusion to another patient or may undergo a therapeutic treatment and/or may be returned to the donor/patient 4.

In a presently preferred embodiment of the blood apheresis system 2 as shown and described in all of the attached drawings, blood is withdrawn from the donor/patient 4 and directed as shown in FIG. 1 through a disposable set 8 which includes an extracorporeal tubing circuit 10 and a blood processing vessel 352 and which defines a completely closed and sterile system. The disposable set 8 is mounted in and/or on the blood component separation device 6 which includes a pump/valve/sensor assembly 1000 for interfacing with the extracorporeal tubing circuit 10, and a channel assembly 200 for interfacing with the disposable blood processing vessel 352.

The channel assembly 200 includes a channel housing 204 which is rotatably interconnected with a rotatable centrifuge rotor assembly 568 which provides the centrifugal forces required to separate blood into its various blood component types by centrifugation. The blood processing vessel 352 is interfitted within or otherwise attached to the channel housing 204. Blood thus flows from the donor/patient 4, through the extracorporeal tubing circuit 10, and into the rotating blood processing vessel 352. The blood within the blood processing vessel 352 is separated into various blood component types and at least one of these blood component types (e.g., platelets, plasma, red blood cells) is preferably continually removed from the blood processing vessel 352 for collection. Separated blood components which are not being collected (e.g., red blood cells, white blood cells, and/or plasma) are also removed from the blood processing vessel 352 and returned to the donor/patient 4 via the extracorporeal tubing circuit 10.

Operation of the blood component separation device 6 is preferably controlled by one or more processors included therein, and may advantageously comprise a plurality of embedded personal computers to accommodate interface with ever-increasing PC user facilities (e.g., CD ROM, modem, audio, networking and other capabilities). Relatedly, in order to assist the operator of the apheresis system 2 with various aspects of its operation, the blood component separation device 6 preferably includes a graphical interface 660.

Disposable Set: Extracorporeal Tubing Circuit

Figure 2A:
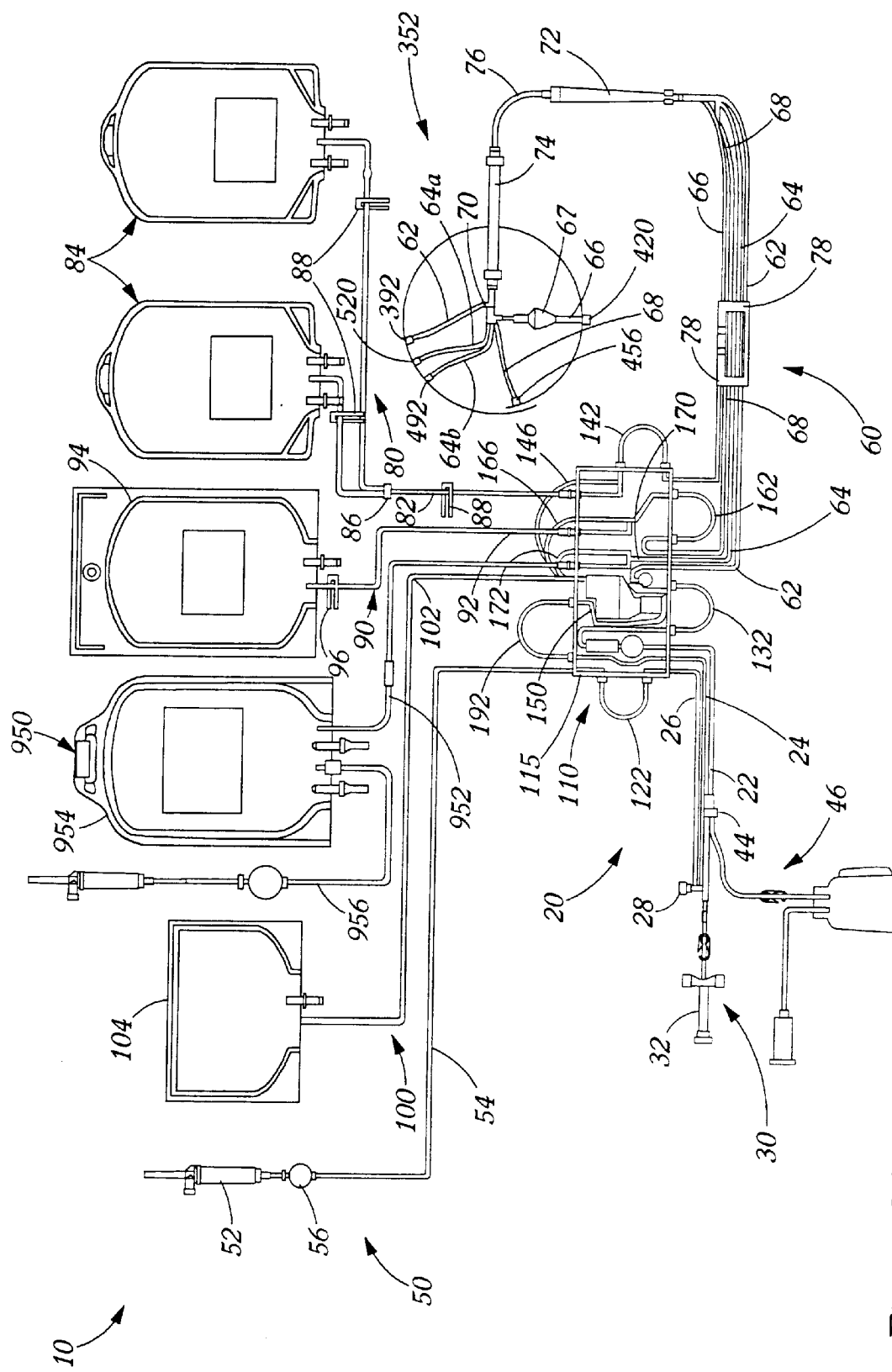
FIGS. 2A–2B illustrate an extracorporeal tubing circuit, cassette assembly, and bag assemblies of the system of FIG. 1.
Figure 2B:
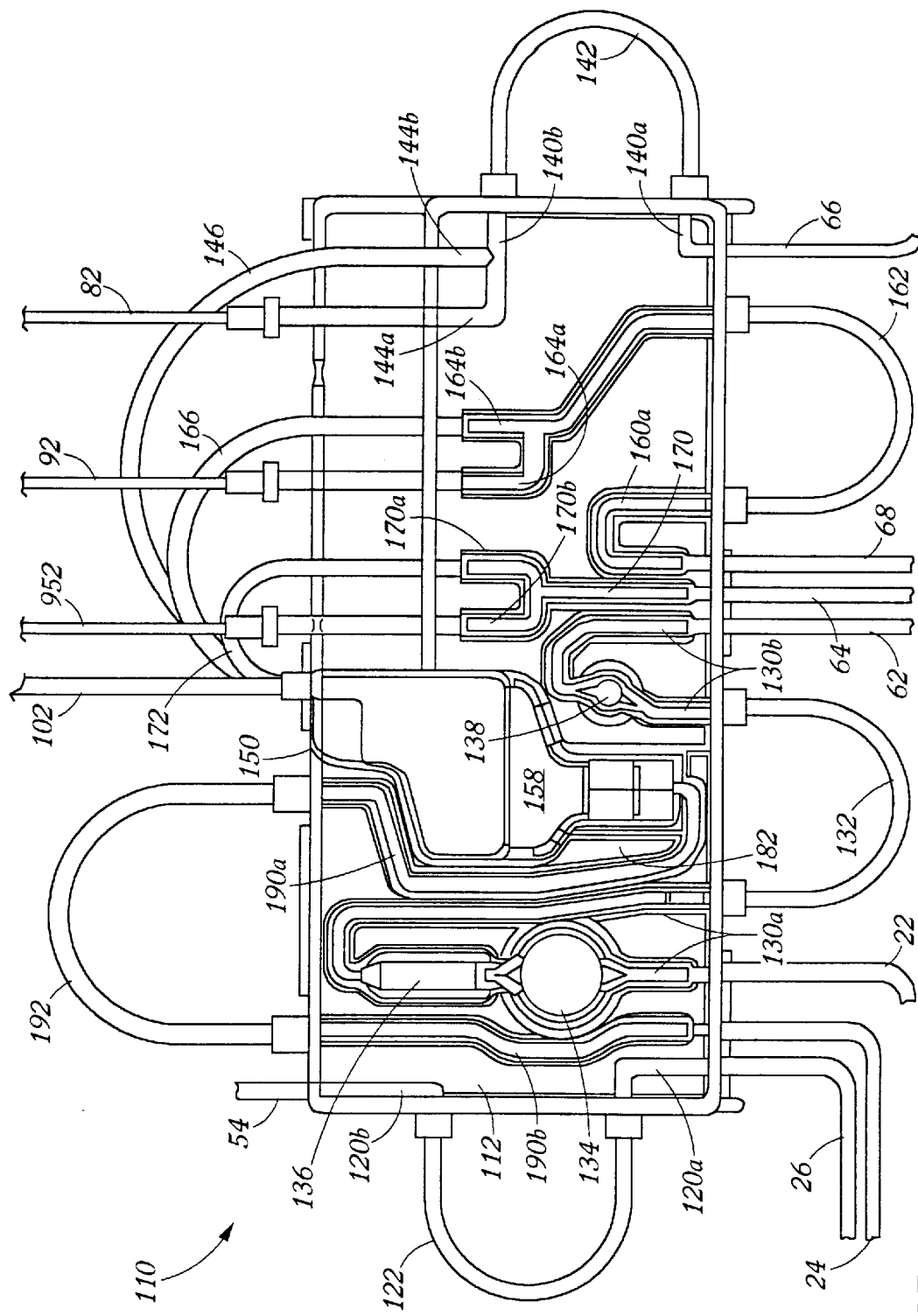
Figure 2C:
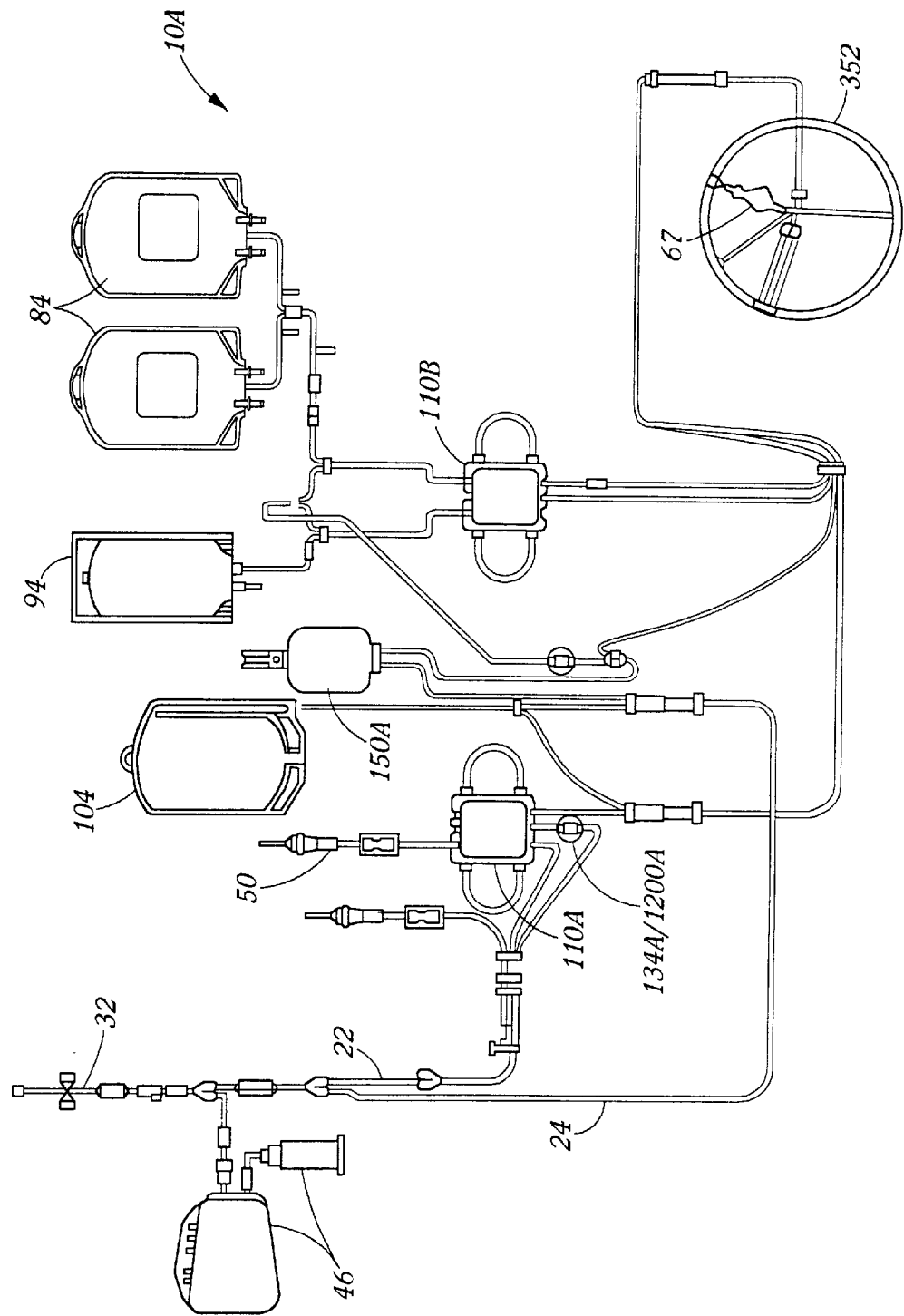
FIG. 2C illustrates an alternative extracorporeal tubing circuit and bag assemblies of an extracorporeal system usable in conjunction with the present invention.

As illustrated in FIGS. 2A, 2B and 2C, two preferred preconnected extracorporeal tubing circuits 10 and 10A are shown which are usable in accordance with the present invention. In the alternative shown in FIGS. 2A and 2B, tubing circuit 10 comprises a cassette assembly 110 and a number of tubing assemblies 20, 50, 60, 80, 90, 100 and/or 950 interconnected therewith. Generally, blood removal/return tubing assembly 20 provides a single needle interface between a donor/patient 4 and cassette assembly 110, and blood inlet/blood component tubing subassembly 60 provides the interface between cassette assembly 110 and blood processing vessel 352. Various combinations and/or permutations of anticoagulant tubing assembly 50, platelet collection tubing assembly 80, plasma collection tubing assembly 90, red blood cell collection assembly 950 and vent bag tubing subassembly 100 may also be interconnected with cassette assembly 110. As will be appreciated, the extracorporeal tubing circuit 10 and blood processing vessel 352 are interconnected to combinatively present a closed, sterilizable disposable set, preferably for a single use.

The blood removal/return tubing assembly 20 shown includes a single needle subassembly 30 interconnected with blood removal tubing 22, blood return tubing 24 and anticoagulant tubing 26 via a common manifold 28. Among other options, blood removal tubing 22 may be provided with a Y-connector 44 interconnected with a blood sampling subassembly 46.

The alternative embodiment shown in FIG. 2C is shown with like numbers representing like elements with certain modifications represented with certain lettered suffixes. For example, the tubing set 10A includes two discrete cassette assemblies 110A and 110B which incorporate some, but not all of the features of the single cassette 110 of FIGS. 2A and 2B. Similarly, the access pressure module/sensor 134A/1200A and the reservoir 150A are discrete elements here and are not resident on or in the cassette 110. This illustrates just one alternative embodiment usable herewith. Indeed, the present invention may be used with a plurality of single needle systems, like those shown here, see also for example, U.S. Pat. No. 5,437,624 which is similar to the FIG. 2C alternative, or even double systems, though these are not shown here.

Nevertheless, a presently preferred cassette assembly 110 such as that shown in FIGS. 2A and 2B will now be described in some detail. As such, cassette assembly 110 includes front and back molded plastic plates 112 and 114 (see FIGS. 4A and 4B) that are hot-welded together to define a rectangular cassette member 115 having integral fluid passageways. The cassette assembly 110 further preferably includes a number of outwardly extending tubing loops interconnecting various integral passageways. The integral passageways are also interconnected to the various tubing assemblies. Specifically, cassette assembly 110 preferably includes a first integral anticoagulant passageway 120a interconnected with the anticoagulant tubing 26 of the blood removal/return tubing assembly 20. The cassette assembly 110 further includes a second integral anticoagulant passageway 120b and a pump-engaging, anticoagulant tubing loop 122 between the first and second integral anticoagulant passageways 120a, 120b. The second integral anticoagulant passageway 120b is interconnected with anticoagulant tubing assembly 50. The anticoagulant tubing assembly 50 includes a spike drip chamber 52 connectable to an anticoagulant source (not shown), anticoagulant feed tubing 54 and a sterilizing filter 56. During use, the anticoagulant tubing assembly 50 supplies anticoagulant to the blood removed from a donor/patient 4 to reduce or prevent any clotting in the extracorporeal tubing circuit 10.

As shown, cassette assembly 110 also preferably includes a first integral blood inlet passageway 130a interconnected with blood removal tubing 22 of the blood removal/return tubing assembly 20. The cassette assembly 110 further includes a second integral blood inlet passageway 130b and a pump-engaging, blood inlet tubing loop 132 between the first and second integral blood inlet passageways 130a, 130b. The first integral blood inlet passageway 130a includes a first pressure-sensing module 134 and inlet filter 136, and the second integral blood inlet passageway 130b includes a second pressure-sensing module 138. The second integral blood inlet passageway 130b is interconnected with blood inlet tubing 62 of the blood inlet/blood component tubing assembly 60.

Blood inlet tubing 62 is also interconnected with input port 392 of blood processing vessel 352 to provide whole blood thereto for processing, as will be described. To return separated blood components to cassette assembly 110, the blood inlet/blood component tubing assembly 60 further includes red blood cell(RBC)/plasma outlet tubing 64, platelet outlet tubing 66 and plasma outlet tubing 68 interconnected with corresponding outlet ports 492 and 520, 456, and 420 of blood processing vessel 352. The RBC/plasma outlet tubing 64 may include a Y-connector 70 to interconnect tubing spurs 64a and 64b. The blood inlet tubing 62, RBC/plasma outlet tubing 64, plasma outlet tubing 68 and platelet outlet tubing 66 all preferably pass through first and second strain relief members 72 and 74 and a braided bearing member 76 therebetween. This advantageously allows for a sealless interconnection such as is taught in the Ito U.S. Pat. No. 4,425,112; inter alia. As shown, multi-lumen connectors 78 can be employed on the various tubing lines.

Platelet outlet tubing 66 also preferably includes a chamber 67 positioned in close proximity to platelet collect port 420 of blood processing vessel 352. During operation, a saturated bed of platelets will form within chamber 67 and advantageously serve to retain white blood cells within chamber 67.

The cassette assembly 110 further preferably includes a pump-engaging, platelet tubing loop 142 interconnecting the first integral platelet passageway 140a and a second integral platelet passageway 140b (see FIG. 2B). The second integral platelet passageway 140b includes first and second spurs 144a and 144b, respectively. The first spur 144a is interconnected with platelet collection tubing assembly 80. The platelet collection tubing assembly 80 can receive separated platelets during operation and includes platelet collector tubing 82 and platelet collection bags 84 interconnected thereto via a Y-connector 86. Slide clamps 88 are provided on platelet collector tubing 82. The second spur 144b of the second integral platelet passageway 140b is interconnected with platelet return tubing loop 146 of the cassette assembly 110 to return separated platelets to a donor/patient 4 (e.g., upon detection of RBC spillover during platelet collection). For such purpose, platelet return tubing loop 146 is interconnected to the top of a blood return reservoir 150 integrally formed by the molded front and back plates 112, 114 of cassette member 115. One or more types of uncollected blood components, collectively referred to as return blood, will cyclically accumulate in and be removed from reservoir 150 during use.

The plasma outlet tubing 68 of blood inlet/blood component tubing assembly 60 interconnects with a first integral plasma passageway 160a of cassette assembly 110. Cassette assembly 110 further includes a pump-engaging, plasma tubing loop 162 interconnecting the first integral plasma passageway 160a and a second integral plasma passageway 160b. The second integral plasma passageway 160b includes first and second spurs 164a and 164b. The first spur 164a is interconnected to the plasma collection tubing assembly 90. The plasma collection tubing assembly 90 may be employed to collect plasma during use and includes plasma collector tubing 92 and plasma collection bag 94. A slide clamp 96 is provided on plasma collector tubing 92. The second spur 164b of the second integral plasma passageway 160b is interconnected to a plasma return tubing loop 166 to return plasma to donor/patient 4. For such purpose, the plasma return tubing loop 166 is interconnected to the top of the blood return reservoir 150 of the cassette assembly 110.

The RBC/plasma outlet tubing 64 of the blood inlet/blood component tubing assembly 60 is interconnected with integral RBC/plasma passageway 170 of cassette assembly 110 (see FIG. 2B). The integral RBC/plasma passageway 170 includes first and second spurs 170a and 170b, respectively. The first spur 170a is interconnected with RBC/plasma return tubing loop 172 to return separated RBC/plasma to a donor/patient 4. For such purpose, the RBC/plasma return tubing loop 172 is interconnected to the top of blood return reservoir 150 of the cassette assembly 110. The second spur 170b may in one alternative embodiment be closed off, or may be connected with an RBC/plasma collection tubing assembly 950 (see FIG. 2A) for collecting RBC/plasma during use. RBC collection tubing assembly 950 preferably includes at least RBC collector tubing 952, and RBC collection reservoir or bag 954. A sterile barrier filter/drip spike assembly 956 may also be included and attached to RBC bag 954.

A vent bag tubing assembly 100 may also preferably be interconnected to the top of blood return reservoir 150 of cassette assembly 110. The vent bag tubing assembly 100 includes vent tubing 102 and a vent bag 104. During use, sterile air present since packaging within cassette assembly 110, and particularly within blood return reservoir 150, may cyclically pass into and back out of vent tubing 102 and vent bag 104. Additional integral passageways, integrated chambers and/or tubing loops could be included in cassette assembly 110 to perform the same or similar functions as the vent bag tubing assembly 100.

A first integral blood return passageway 190a is preferably interconnected to the outlet 182 of blood return reservoir 150, and is further interconnected to a second integral blood return passageway 190b via a pump-engaging, blood return tubing loop 192. The second integral blood return passageway 190b is interconnected with the blood return tubing 24 of the blood removal/return tubing assembly 20 to return blood components to the donor/patient 4 via needle assembly 30.

Tubing assemblies 20, 50, 60, 80, 90, 100 and 950 and cassette assembly 110 are preferably made from PVC tubing and plastic components that permit visual observation and monitoring of blood/blood components therewithin during use. It should be noted that thin-walled PVC tubing (e.g., less than about 0.023 inch) may be employed for approved, sterile docking (i.e., the direct connection of two pieces of tubing) for platelet collector tubing 82, plasma collector tubing 92 and RBC/plasma collector tubings 952. In keeping with one preferred embodiment of the invention, all tubing is preconnected before sterilization of the disposable to assure that maximum sterility of the system is maintained. Alternatively, thicker-walled PVC tubing (e.g., about 0.037 inch or more) may be employed for approved, sterile docking for these tubings and is otherwise preferably utilized for pump-engaging tubing loops 132, 142, 162 and 192.

Pump/Valve/Sensor Assembly

Figure 3:
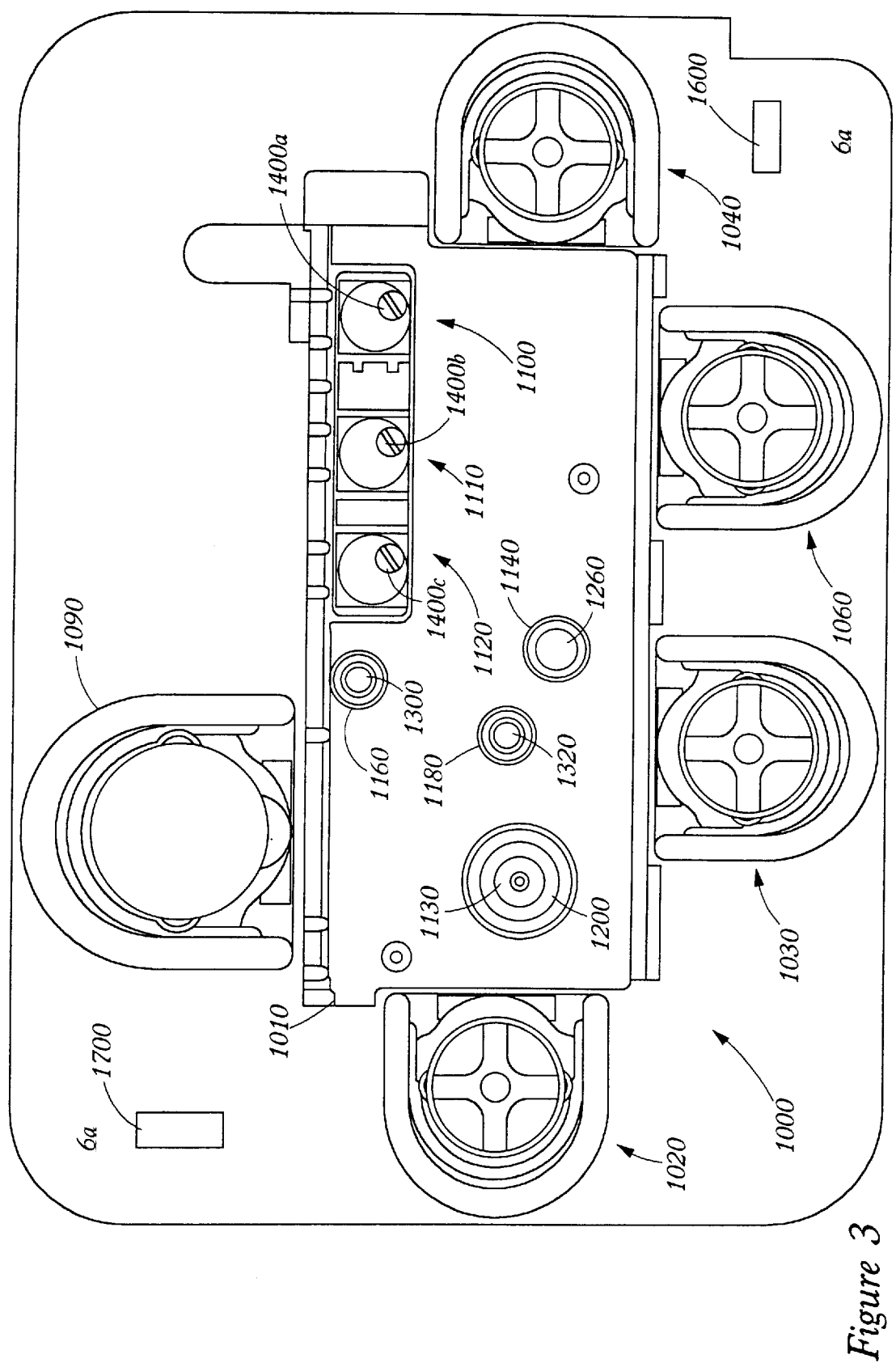
FIG. 3 is a front view of a pump/valve/sensor assembly for the system of FIG. 1.

As noted, cassette assembly 110 may be mounted upon and operatively interface with the pump/valve/sensor assembly 1000 of blood component separation device 6 during use. The pump/valve/sensor assembly 1000 as illustrated in FIG. 3 preferably includes a cassette mounting plate 1010, and a number of peristaltic pump assemblies, flow divert valve assemblies, pressure sensors and ultrasonic level sensors interconnected to face plate 6a of blood collection device 6 for pumping, controlling and monitoring the flow of blood and blood components through extracorporeal tubing circuit 10 during use.

More particularly, anticoagulant pump assembly 1020 is provided to receive anticoagulant tubing loop 122, blood inlet pump assembly 1030 is provided to receive blood inlet tubing loop 132, platelet pump assembly 1040 is provided to receive platelet tubing loop 142, plasma pump assembly 1060 is provided to receive plasma tubing loop 162, and blood return pump assembly 1090 is provided to receive blood return tubing loop 192. Each of these peristaltic pump assemblies includes a respective rotor and raceway between which the corresponding tubing loop is positioned to control the passage and flow rate of the corresponding fluid.

Platelet divert valve assembly 1100 is provided to receive platelet collector tubing 82 and platelet return tubing loop 146, plasma divert valve assembly 1110 is provided to receive plasma collector tubing 92 and plasma return tubing loop 166, and RBC/plasma divert valve assembly 1120 is provided to receive RBC/plasma return tubing loop 172 and RBC/plasma collector tubing 952. Platelet divert valve assembly 1100, plasma divert valve assembly 1110 and RBC/plasma divert valve assembly 1120 each preferably include a rotary occluding member 1400a, 1400b and 1400c that is selectively positionable between respective stationary occluding walls for diverting fluid flow through one tubing of the corresponding pairs of tubings.

Pressure sensors 1200 and 1260 (See also FIGS. 4A and 4B) are provided within pump/valve/sensor assembly 1000 to operatively engage the first and second pressure-sensing modules 134 and 138 of cassette assembly 110 through openings 1130 and 1140 of cassette mounting plate 1100. Similarly, ultrasonic level sensors 1300 and 1320 are provided to operatively engage the blood return reservoir 150 of cassette assembly 110 through openings 1160 and 1180 of cassette mounting plate 1010.

Figure 4A:
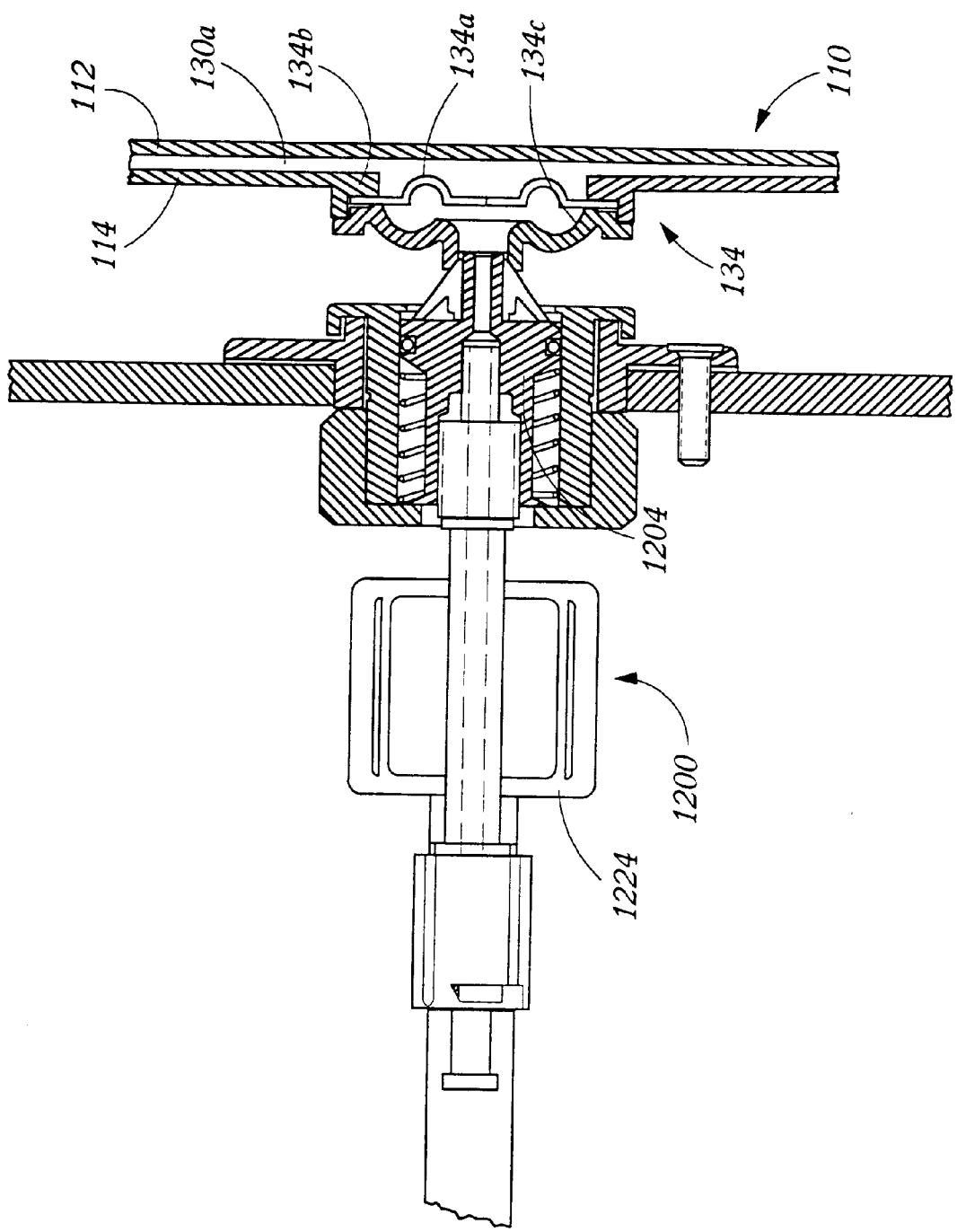
FIGS. 4A–4B are cross-sectional side views of first and second pressure sensing modules of the extracorporeal tubing circuit of FIGS. 2A–2B coupled with corresponding pressure sensors of the pump/valve/sensor assembly of FIGS. 1 and 3.
Figure 4B:
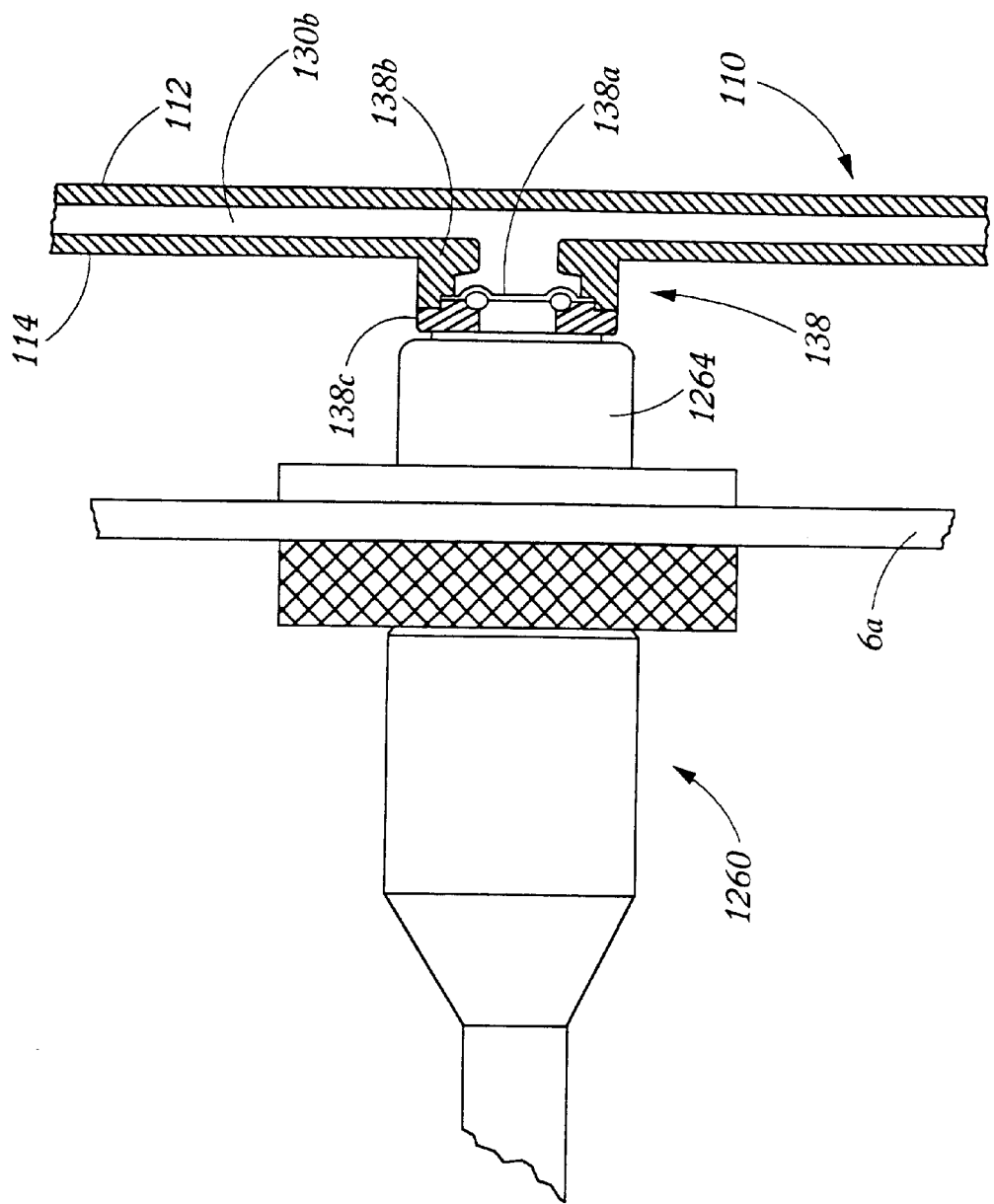

As shown in FIGS. 4A and 4B, presently preferred embodiments of first and second pressure sensing modules 134, 138 of cassette assembly 110 each comprise a circular diaphragm 134a, 138a positioned on a raised cylindrical seat 134b, 138b formed into the back plate 114 of cassette assembly 110 with a ring-shaped, plastic diaphragm retainer 134c, 138c hot-welded to the raised cylindrical seats 134b, 138b to establish a seal therebetween. This arrangement allows the diaphragms 134a, 138a to be directly responsive to the fluid pressures within the first and second integral blood inlet passageways 130a, 130b, respectively, and pressure sensors 1200, 1260 to directly access the diaphragms 134a, 138a through the ring-shaped retainers 134c, 138c. By monitoring the diaphragms 134a, 138a, the pressure sensors 1200, 1260 can monitor the fluid pressure within the first and second integral blood inlet passageways 130a, 130b. In this regard, it should also be noted that since first integral blood inlet passageway 130a is in direct fluid communication with blood removal tubing 22, and since blood removal tubing 22 and blood return tubing 24 are fluidly interconnected via the common manifold 28, the first pressure sensing module 134 will be responsive to and first pressure sensor 1200 will actually sense the substantially common pressure in both the blood removal tubing 22 and blood return tubing 24 during operation.

With further regard to the preferred first pressure sensing module 134 and first pressure sensor 1200, FIG. 4A illustrates a preferred coupling arrangement that allows for the sensing of positive and negative pressure changes (i.e., causing outward and inward flexure of diaphragm 134a). More details of a preferred sensing apparatus of this type can be found in the disclosure of U.S. Pat. No. 5,795,317 inter alia. A Even so, it may be noted here that a pressure sensing transducer 1224 engages air channel member 1204 to sense positive and negative pressure changes within sensing module 134 and provide an output signal in response thereto during use. As will be further described, the output signal of pressure transducer 1224 can be employed to control the operation of blood inlet pump 1030 and blood return pump 1090 during operation.

With regard to the preferred second pressure sensing module 138 and second pressure sensor 1260, FIG. 4B illustrates a direct contact coupling approach that allows for sensing of positive pressure changes (i.e., causing outward flexure of diaphragm 138a). Such contact coupling facilitates loading since the precise position of the diaphragm 138a relative to the second pressure sensor 1260 is not critical. As above, more details of a preferred pressure sensor can be found in U.S. Pat. No. 5,795,317; inter alia. Pressure transducer 1264 provides an output signal responsive to positive pressure changes acting upon diaphragm 138a.

Operation of Extraeoporeal Tubing Circuit and Pump/Valve/Sensor Assembly

In an initial priming mode of operation, blood return pump 1090 may be operated in reverse to transfer a priming solution, which in a preferred embodiment may be whole blood, through blood removal/return tubing assembly 20, integral blood return passageway 190, blood return tubing loop 192 and into reservoir 150. Contemporaneously and/or prior to the reverse operation of blood return pump 1090, anticoagulant peristaltic pump 1020 may be operated to prime and otherwise provide anticoagulant from anticoagulant tubing assembly 50, through anticoagulant integral passageway 120, and into blood removal tubing 22 and blood return tubing 24 via manifold 28. When lower level ultrasonic sensor 1320 senses the presence of the priming solution or whole blood in reservoir 150 a signal is provided and blood component separation device 6 stops blood return peristaltic pump 1090. During the priming mode blood inlet pump 1030 is also operated to transfer priming solution or blood into blood inlet integral passageway 130, through blood inlet tubing loop 132 and into blood inlet/blood component tubing assembly 60 to prime the blood processing vessel 352.

Then, in the preferred embodiment blood processing mode, the blood inlet peristaltic pump 1030, platelet peristaltic pump 1040 and plasma peristaltic pump 1060 are operated continuously, and the occluding members 1400a, 1400b, 1400c are positioned for collection or return of corresponding blood components, as desired. In the preferred single needle system, during a blood removal submode, blood return peristaltic pump 1090 is not operated so that whole blood will pass into blood removal/return tubing assembly 20 and be transferred to processing vessel 352 via the cassette assembly 110 and blood inlet/blood component tubing assembly 60. In the blood removal submode, all separated blood components are transferred from the processing vessel 352 to cassette assembly 110, and uncollected components are passed into and accumulate in reservoir 150 up to a predetermined level at which upper level ultrasonic sensor 1300 provides signals used by blood component separation device 6 to end the blood removal submode and initiate a blood return submode. More particularly, the blood return submode is initiated by forward operation of blood return peristaltic pump 1090. In this regard, it should be appreciated that in the blood return submode the volume transfer rate of return blood through blood return tubing loop 192 utilizing blood return peristaltic pump 1090 is established by blood component separation device 6, according to a predetermined protocol, to be greater than the volume transfer rate through blood inlet tubing loop 132 utilizing blood inlet peristaltic pump 1030. As such, the accumulated blood in reservoir 150 is transferred into the blood return tubing of blood removal/return tubing assembly 20 and back into the donor/patient 4. When the accumulated return blood in reservoir 150 is removed down to a predetermined level, lower level ultrasonic sensor 1320 will fail to provide signals to blood component separation device 6, whereupon blood component separation device 6 will automatically stop blood return peristaltic pump 1090 to end the blood return submode. This automatically serves to reinitiate the blood removal submode since in the preferred embodiments the blood inlet peristaltic pump 1030 continuously operates.

During the blood processing mode, pressure sensor 1200 senses negative/positive pressure changes within the blood removal tubing 22 and blood return tubing 26 via first integral blood inlet passageway 130a. Such monitored pressure changes are communicated to blood component separation device 6 which in turn controls blood inlet pump 1030 and return pump 1090 so as to maintain fluid pressures within predetermined ranges during the blood removal and the blood return submodes. Specifically, in one embodiment, during the blood removal submode, if a negative pressure is sensed that exceeds (i.e., is less than) a predetermined negative limit value, then blood component separation device 6 will slow down operation of blood inlet pump 1030 until the sensed negative pressure is back within an acceptable range. During the blood return submode, if a positive pressure is sensed that exceeds (i.e., is greater than) a predetermined positive limit value, then blood component separation device 6 will slow down operation of blood return pump 1090 until the sensed positive pressure is back within an acceptable range.

In another embodiment, separation device 6 will pause all pumps when the pressure reaches an alarm point. In the draw cycle, device 6 can then hold this pause until the pressure rises above the negative alarm point or another discrete set point (such as −50 mmHg, for example). An audible squeeze beep sound or other warning alarm signal, message or the like can be emitted by device 6 during this pump pause at least so long as the pressure remains below the alarm or other set point. Device 6 can further set or have a set time limit (for a period of for example 6 seconds) for an automatic resolution during this pause after which, if there is no resolution, a regular/full alarm condition occurs. Resolution is the pressure rise to above the alarm or other pre-selected set point. The regular/full alarm condition involves complete stoppage of all pumps and requires operator intervention to re-start the pumps. The advantage in this embodiment is to minimize operator intervention with pressure alarms which may automatically resolve or may be resolved with mere donor/patient intervention by the donor/patient squeezing his or her fist in response to the squeeze beep warning signal. This fist squeezing could raise the pressure in the donor/patient's access vasculature and/or could otherwise properly expand a collapsed vein to establish proper seating of the access/draw needle therein.

Note, as mentioned above, certain access/draw pressure conditions signify no flow or improper flow characteristics which may need to be addressed by an operator. However, some of these pressure conditions may be resolved prior to operator intervention by the donor/patient (fist squeezing, e.g.), or by the machine (a pump pause or slowing may allow the pressure in the donor/patient's vasculature to raise). Thus, in the known example where the access/draw needle may become improperly seated or blocked within the donor/patient access site, the access/draw pressures sensed by the extracorporeal processing system can be interpreted as indicating the problem and then to, activating an alarm of a warning nature for donor/patient intervention as well as initiating pump and/or other fluid flow controls such as slowing or stopping the flow or flows or pump or pumps. If either of these initial procedures fails to resolve the situation (or if an ultimate alarm point is reached), then the processing system may signal a distinct alarm for operator intervention.

In another embodiment which may be used with either alternative described above, device 6 may be configured to interpret a particular quantity of warning alarms occurring within a particular time period as a trigger for setting a regular/full alarm. Thus, whether device 6 merely slows the pumps or pauses them for a period of time as a warning alarm in response to a low pressure signal, if the warning alarm occurs too many times during a particular time period, then device 6 goes to regular/full alarm and stops the pumps and alerts the operator to intervene and check certain elements of the system. In combination with the second alternative described above (where the pumps pause for a particular time period), this alternative provides for a full alarm condition even if the pressure resolves (i.e., rises above the alarm or other set point) each time within the designated period. An example of a quantity per period under this alternative is three warnings occurring in three minutes. The advantage is that even if resolution appears to be automatically or with donor/patient assistance readily gained, something more serious may still be wrong at least insofar as the operator should intervene to ensure proper needle placement in the vein or to check whether the pressure cuff (if used, see FIG. 10, e.g.) is properly inflated or to make adjustments to the donor flow rate.

A third alternative embodiment which may be used alone or in any combination with the above embodiments involves a single needle adaptation. As described hereinabove, and as understood in the art, in single needle systems generally, separated blood components destined for return to the donor/patient are first accumulated in a reservoir, such as reservoir 150 of the cassette 110 described above. Thus, during blood processing operation, blood is cyclically accumulated in the reservoir and then cyclically pumped back to the donor/patient. In a pressure alarm situation, the accumulated blood components in the reservoir may be pumped back to the donor/patient strategically in response to the alarm as follows. If the pressure drops to the warning point (or within a certain pre-selected point of the warning or full alarm point) and the draw cycle (or reservoir 150 accumulation cycle) is greater than a pre-selected percentage of completion (e.g., 90%), then the warning alarm condition may include a switch to the blood return mode by switching on the blood return pump (such as pump 1090, hereinabove) and pausing (or slowing) all of the other pumps according to the above-described alternative embodiments. This embodiment may either be used alone or with any one or more of the other alternatives described herein, such as for example counting against the set quantity per period alternative (the three times in three minutes example, above). Other options may also be configured herewith, as for example, disabling this switch to return in certain phases of a blood processing procedure (for example, not allowing a switch to return during the first five draw cycles or any other time as may be appropriate).

In yet another alternative embodiment particularly involving a fluid chamber such as chamber 67 (see FIGS. 1 and 2A) preferred embodiments of which being described in various U.S. and corresponding foreign patents, such as U.S. Pat. Nos. 5,674,173; 5,722,926; 5,906,570; 5,913,768; 5,939,319 and 5,951,877; inter alia, a resolvable low access pressure situation will preferably not be permitted to interrupt the flow of components and fluids thereinto and therethrough. Thus, a warning alarm condition as generally described above may be made to stop or pause all pumps (according to the selected alternative above) except for the platelet pump (such as pump 1040 hereinabove) which may be made to continue to run for a pre-selected period (for example, two seconds) during which time the low access pressure condition will either resolve (i.e., rise above the alarm or other set point) or the regular/full alarm will then occur and device 6 will stop all pumps for operator intervention.

In the above-described alternative embodiments, generally only one alarm pressure point is involved. This is distinctive from many prior, conventional systems which incorporate a warning alarm point as an adjunct to an ultimate low pressure alarm point at which the regular/full alarm condition is met. In these prior, conventional systems the warning alarm point is some set level higher than the ultimate low pressure point such that as the access/draw pressure falls from the desirable operation level, it first reaches the warning alarm point and the processing device can then signal with a squeeze beep or other message to the operator and/or the donor/patient to try to raise the access pressure as by squeezing of the donor/patient fist. Then, in these prior, conventional systems either the access pressure is raised (or at least stopped from falling) during which time the blood processing machine continues to operate (even if at reduced rates), or the access pressure continues to fall until it reaches the ultimate low level point whereupon the processing device signals the regular/full alarm condition and stops all flows.

In contrast, the above alternatives do not require a bottom or ultimate low pressure level point for activation of the regular/full alarm. Rather, the regular/full alarm will instead be signaled by the reaching the end of the resolution pause period or the pre-selected quantity of warnings per period (and/or the limits of the other options as described herein).

Even so, the above-described alternatives of the present invention may also be incorporated with an ultimate low level pressure point as well. Thus, when there is a failure to resolve in either the pause period or the quantity per period has been reached, device 6 may instead of going to a regular/full alarm condition including full pump stoppage may instead run the pumps at an adjusted percentage of full operational speeds (or could stop some pumps and/or maintain others such as the platelet pump as above). This would prevail until resolution or operator intervention (an intermediate alarm condition could be signaled here) or until the ultimate low pressure level is reached at which point the pumps are all stopped and the regular/full alarm condition is signaled. Note, an adjusted percentage of full speed option here is preferably usable on/with systems which use a warning alarm point in addition to an ultimate low alarm point; thus, the adjusted percentage option described here would preferably only become effective in the pressure interval after the warning point is reached with the pause period expired, but only before the ultimate low alarm point is reached. Often, the adjusted percentage will not be preferable because the warning alarm point will be set at a low flow/low pressure level such that the pump(s) will preferably remain paused until resolution, or if there is no resolution, then merely stopped. Re-starting such pumps without resolution would likely only exacerbate the situation/problem.

A few variations of what the warning alarm limits which would trigger the selected alternative alarm occurrences described above are also contemplated by the present invention. For example, the access or draw pressure alarm limit in prior, conventional systems was usually set at or around an ultimate low pressure limit of −350 mmHg. This limit may have had an empirical basis. Warning limits may have been set there also, or at some incremental higher level. Nevertheless, a presently preferred alarm limit may be adjusted or adjustable in view of certain pre-selected parameters. In particular and in the case where there is a single needle having a single pressure sensor (such as sensor 1200 in a preferred embodiment as described above) applied to sense both the inlet/draw pressure as well as the return pressure, certain relationships can be used to adjust both the draw and the return limits. Thus, an access/draw alarm pressure limit may be defined by the equation:

$$\text{Draw Alarm Limit} = \text{Config} + 75 - 0.3309 * Q_{in}/(1-H_{in}) - 0.3026 * Q_n/(1-H_n)$$

where,
Config=a configuration pre-selected pressure (e.g., −250 mmHg.)
$Q_{in}$=flow rate in the inlet tubing line;
$H_{in}$=Hematocrit in the inlet tubing line;
$Q_n$=flow rate in the needle; and
$H_n$=Hematocrit in the needle.

The above equation is in part theoretically derived depending upon geometry (i.e. the lengths and diameters of the inlet tubing and needle. As such, this equation resembles a pipe flow equation. It is also dependent on the viscosity of the blood flowing there through. The equation takes the pressure drop due to the needle, the inlet line and hematocrit into account. The above equation is presently preferred for platelet collection tubing sets.

A similar presently preferred equation for RBC/plasma collection tubing sets is as follows:

$$\text{Draw Alarm Limit} = \text{Config} + 75 - 0.3309 * Q_{in}/(1-H_{in}) - 0.5602 * Q_n/(1-H_n)$$

where the variables are defined as above. The coefficients here presume an 18 gauge (ga) needle is used. In both of the above equations, a maximum negative limit of −350 mmHg is preferably imposed, partly in deference to historical empirical development.

Similar maximum return pressure alarm limits may be calculated by device 6 such that for platelet tubing sets:

Return Alarm Limit=Config−50−0.3309*$Q_{in}$/(1−$H_{in}$)−0.3026*$Q_n$/(1−$H_n$);

and for RBC/plasma tubing sets:

Return Alarm Limit=Config−50−0.3309*$Q_{in}$/(1−$H_{in}$)−0.5602*$Q_n$/(1−$H_n$);

where the above definitions and assumptions remain except the config limit which would preferably be changed to a value such as +310 mmHg, and the maximum positive limit being set at +400 mmHg as an override of the equation(s). Further, $Q_n$ is negative in the return equations, and the hematocrit being returned is determined by monitoring the hematocrit in the reservoir 150 in the previous draw cycle. These equations also take into account whether there may be recirculation in the draw line as pulling from the return line.

Returning now to the general description of the blood processing operation, the second pressure sensor 1260 monitors the positive pressure within the second integral blood inlet passageway 130b and blood inlet tubing 62 after the inlet pump 1030. If such sensed positive pressure exceeds a predetermined maximum value, blood component separation device 6 will initiate appropriate responsive action, including, for example, slowing or stoppage of the centrifuge and peristaltic pumps.

During the blood processing mode, blood component separation device 6 controls the operation of anticoagulant pump 1020 according to a predetermined protocol and responsive to signals provided by AC sensor 1700 (e.g., FIG. 3) which may indicate a depleted anticoagulant source. Also, blood component separation device 6 also controls the operation of divert assemblies 1100, 1110, 1120 according to predetermined instructions and further pursuant to any detect signals provided by an RBC spillover detector 1600 (FIG. 3). In the latter regard, if an RBC spillover in the separated platelet stream is detected, blood component separation device 6 will automatically cause occluder member 1400a to divert the separated platelet stream to the return reservoir 150 until the RBC spillover has cleared, thereby keeping red blood cells from undesirably passing into platelet collector tubing assembly 80.

In normal operation, whole blood will pass through needle assembly 30, blood removal tubing 22, cassette assembly 110 and blood inlet tubing 62 to processing vessel 352. The whole blood will then be separated in vessel 352. A platelet stream will pass out of port 420 of the vessel, through platelet tubing 66, back through cassette assembly 110, and will then be either collected in collector assembly 80 or diverted to reservoir 150. Similarly, separated plasma will exit vessel 352 through port 456 to plasma tubing 68 back through cassette assembly 110, and will then either be collected in plasma tubing assembly 90 or diverted to reservoir 150. Further, red blood cells and plasma (and potentially white blood cells) may pass through ports 492 and 520 of vessel 352 through RBC/plasma tubing 64, through cassette assembly 110 and into reservoir 150. Alternatively, during an RBC collection procedure described generally hereinbelow, separated RBCs will be delivered to RBC/plasma collector tubing assembly 950 through tubing 952 for collection.

As noted above, when uncollected platelets, plasma, and RBC/plasma (and potentially white blood cells) have accumulated in reservoir 150 up to upper ultrasonic level sensor 1300, operation of return peristaltic pump 1090 will be initiated to remove the noted components from reservoir 150 and transfer the same back to the donor/patient 4 via the return tubing 24 and needle assembly 20. When the fluid level in the reservoir 150 drops down to the level of the lower ultrasonic level sensor 1320, the return peristaltic pump 1090 will automatically turn off reinitiating the blood removal submode. The cycle between blood removal and blood return submodes will then continue until a predetermined amount of platelets or other collected blood components have been harvested.

In one embodiment, reservoir 150 and upper and lower ultrasonic sensors 1300 and 1320 are provided so that, during the blood processing mode, approximately 50 milliliters of return blood will be removed from reservoir 150 during each blood return submode and accumulated during each blood removal submode. Relatedly, in such embodiment, lower and upper level triggering by ultrasonic sensors 1300 and 1320 occurs at fluid volumes of about 15 milliliters and 65 milliliters, respectively, within reservoir 150. For such embodiment, it is also believed desirable to provide for a volume transfer operating rate range of about 30 to 300 milliliters/minute through blood return tubing loop 192 utilizing return pump 1090, and a volume transfer operating rate range of about 20 to 140 milliliters/minute through blood inlet tubing loop 132 utilizing inlet pump 1030. Additionally, for such embodiment the maximum pressure limits may be altered slightly such that a negative pressure limit of about −250 mmHg and positive pressure limit of about 350 mmHg may be appropriate for controlling the speed of inlet pump 1030 and return pump 1090, respectively, in response to the pressures sensed in first pressure sensing module 134. A positive pressure limit of about 1350 mmHg within second sensing module 138 is believed appropriate for triggering slow-down or stoppage of the centrifuge and pumps.

Channel Housing

Figure 5:
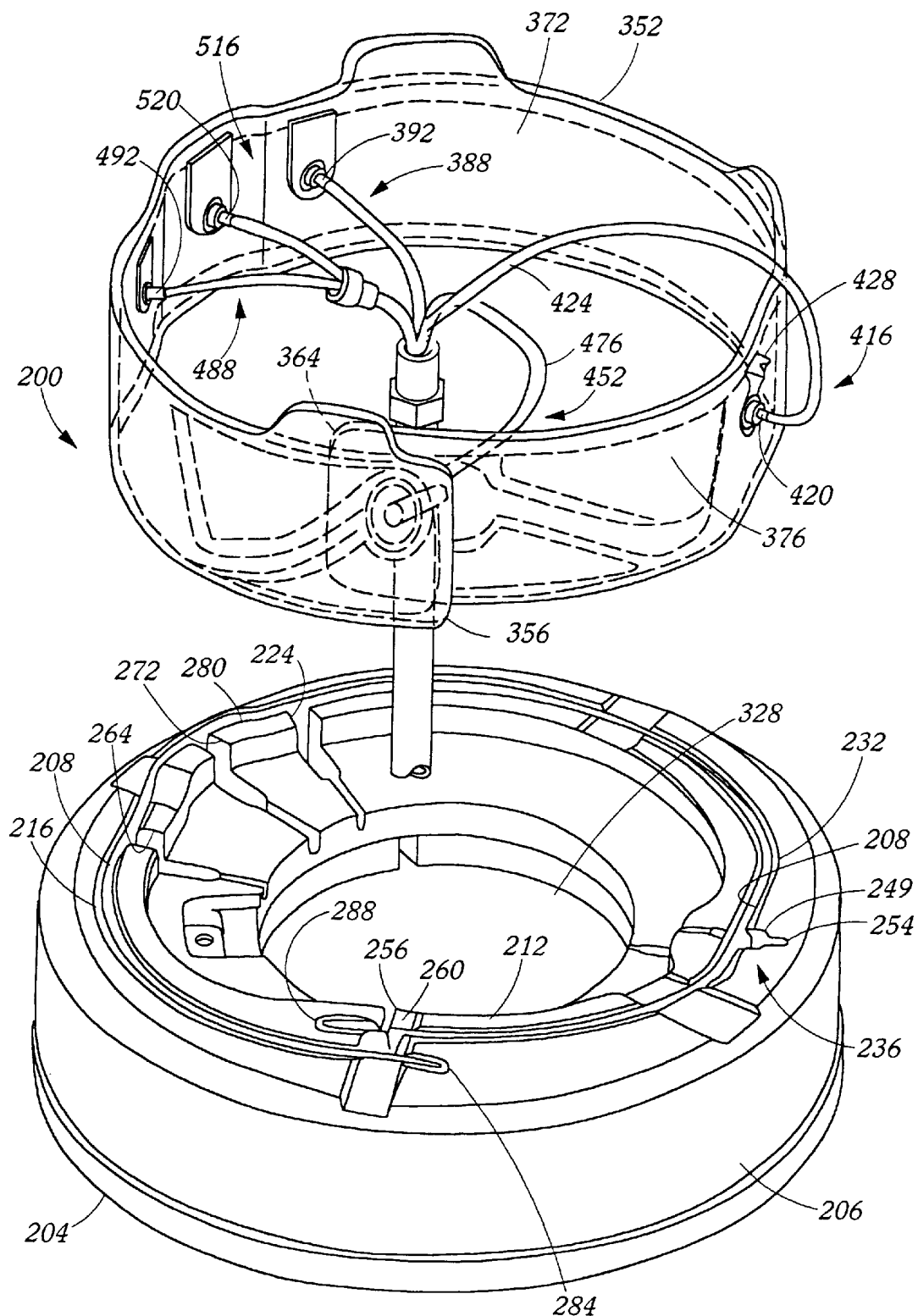
FIG. 5 is an isometric view of the channel assembly and a portion of the extracorporeal tubing circuit of the system of FIG. 1.
Figure 6:
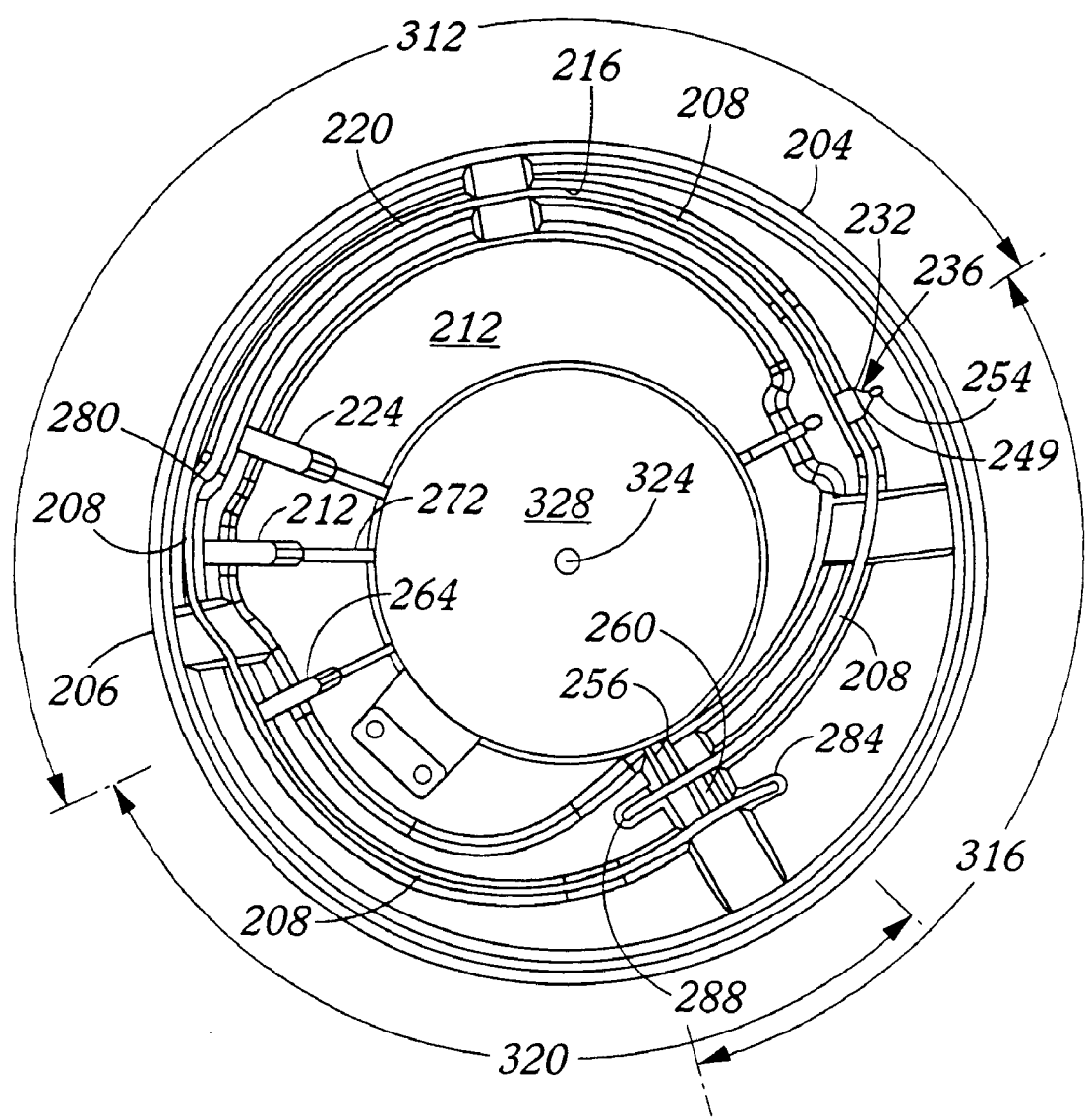
FIG. 6 is a top view of the channel housing from the channel assembly of FIG. 5.

A preferred channel assembly 200 is illustrated in FIGS. 1, 5 and 6 and includes a channel housing 204 which is disposed on the rotatable centrifuge rotor assembly 568 (see FIG. 1) and which receives a disposable blood processing vessel 352. Referring more specifically to FIGS. 5–6, the channel housing 204 has a generally cylindrically-shaped perimeter 206 with a diameter of preferably no more than about 10 inches to achieve a desired size for the blood component separation device 6 (e.g., to enhance its portability). An opening 328 extends longitudinally through the channel housing 204 and contains an axis 324 (shown as a center dot in FIG. 6) about which the channel housing 204 rotates. The channel housing 204 may be formed from materials such as delrin, polycarbonate, or cast aluminum and may include various cut-outs or additions to achieve weight reductions and/or rotational balance.

The primary function of the channel housing 204 is to provide a mounting for the blood processing vessel 352 such that the blood may be separated into the blood component types in a desired manner. In this regard, the channel housing 204 includes a generally concave channel 208 in which the blood processing vessel 352 is positioned. The channel 208 is principally defined by an inner channel wall 212, an outer channel wall 216 which is radially spaced from the inner channel wall 212, and a channel base 220 which is positioned therebetween. The channel 208 also extends from a first end 284 generally curvilinearly about a rotational axis 324 of the channel housing 204 to a second end 288 such that a continuous flow path may be provided about the rotational axis 324.

The blood processing channel vessel 352 is removably disposed within the channel 208. Generally, the channel 208 desirably allows blood to be provided to the blood processing vessel 352 during rotation of the channel housing 204, to be separated into its various blood component types by centrifugation, and to have various blood component types removed from the blood processing vessel 352 during rotation of the channel housing 204. For instance, the channel 208 is configured to allow for the use of high packing factors (e.g., generally a value reflective of how "tightly packed" the red blood cells and other blood component types are during centrifugation). Moreover, the channel 208 also desirably interacts with the blood processing vessel 352 during centrifugation (e.g., by maintaining a desired contour of the blood processing vessel 352).

The above-identified attributes of the channel 208 are provided primarily by its configuration. In this regard, the channel housing 204 includes a blood inlet slot 224 which is generally concave and which intersects the channel 208 at its inner channel wall 212 in substantially perpendicular fashion. A blood inlet port assembly 388 of the disposable set 10 which leads to the interior of the blood processing vessel 352 is disposed in this blood inlet slot 224 such that blood from the donor/patient 4 may be provided to the blood processing vessel 352 when in the channel 208.

As illustrated in FIGS. 5–6, an RBC dam 232 of the channel 208 is disposed in a clockwise direction from the blood inlet slot 224 and whose function is to preclude RBCs and other large cells such as WBCs from flowing in a clockwise direction beyond the RBC dam 232. Generally, the surface of the RBC dam 232 which interfaces with the fluid containing volume of the blood processing vessel 352 may be defined as a substantially planar surface or as an edge adjacent the collect well 236. At least in that portion of the channel 208 between the blood inlet port 224 and the RBC dam 232, blood is separated into a plurality of layers of blood component types including, from the radially outermost layer to the radially innermost layer, red blood cells ("RBCs"), white blood cells ("WBCs"), platelets, and plasma. The majority of the separated RBCs are removed from the channel 208 through an RBC outlet port assembly 516 which is disposed in an RBC outlet slot 272 associated with the channel 208, although at least some RBCs may be removed from the channel 208 through a control port assembly 488 which is disposed in a control port slot 264 associated with the channel 208.

The RBC outlet port slot 272 is disposed in a counter-clockwise direction from the blood inlet slot 224, is generally concave, and intersects the channel 208 at its inner channel wall 212 in substantially perpendicular fashion. An RBC outlet port assembly 516 to the interior of the blood processing vessel 352 is disposed in this RBC outlet slot 272 such that separated RBCs from the apheresis procedure may be continually removed from the blood processing vessel 352 when in the channel 208 (e.g., during rotation of the channel housing 204).

The control port slot 264 is disposed in a counterclockwise direction from the RBC outlet slot 272, is generally concave, and intersects the channel 208 at its inner channel wall 212 in substantially perpendicular fashion. A control port assembly 488 to the interior of the blood processing vessel 352 is disposed in the control port slot 264.

The portion of the channel 208 extending between the control port slot 264 and the RBC dam 232 may be characterized as the first stage 312 of the channel 208. The first stage 312 is configured to remove primarily RBCs from the channel 208 by utilizing a reverse flow in relation to the flow of platelet-rich plasma in the channel 208 which is in a clockwise direction. In this regard, the outer channel wall 216 extends along a curvilinear path from the RBC dam 232 to the blood inlet slot 224 generally progressing outwardly away from the rotational axis 324 of the channel housing 204. That is, the radial disposition of the outer channel wall 216 at the RBC dam 232 is less than the radial disposition of the outer channel wall 216 at the blood inlet slot 224. The portion of the RBC outlet slot 272 interfacing with the channel 208 is also disposed more radially outwardly than the portion of the blood inlet slot 224 which interfaces with the channel 208.

In the first stage 312, blood is separated into a plurality of layers of blood component types including, from the radially outermost layer to the radially innermost layer, red blood cells ("RBCs"), white blood cells ("WBCs"), platelets, and plasma. As such, the RBCs sediment against the outer channel wall 216 in the first stage 312. By configuring the RBC dam 232 such that it is a section of the channel 210 which extends further inwardly toward the rotational axis 324 of the channel housing 204, this allows the RBC dam 232 to retain separated RBCs and other large cells as noted within the first stage 312. That is, the RBC dam 232 functions to preclude RBCs from flowing in a clockwise direction beyond the RBC dam 232.

Separated RBCs and other large cells are removed from the first stage 312 utilizing the above-noted configuration of the outer channel wall 216 which induces the RBCs and other large cells to flow in a counterclockwise direction (e.g., generally opposite to the flow of blood through the first stage 312). Specifically, separated RBCs and other large cells flow through the first stage 312 along the outer channel wall 216, past the blood inlet slot 224, and to an RBC outlet slot 272. In order to reduce the potential for counterclockwise flows other than separated RBCs being provided to the control port assembly 488 disposed in the control port slot 264 such that there is a sharp demarcation or interface between RBCs and plasma proximate the control port slot 264, a control port dam 280 of the channel 208 is disposed between the blood inlet slot 224 and the RBC outlet slot 272. That is, preferably no WBCs nor any portion of a buffy coat, disposed radially adjacent to the separated RBCs, is allowed to flow beyond the control port dam 280 and to the control port slot 264. The "buffy coat" includes primarily WBCs, lymphocytes, and the radially outwardmost portion of the platelet layer. As such, substantially only the separated RBCs and plasma are removed from the channel 208 via the RBC control slot 264 to maintain interface control as noted.

The flow of RBCs to the control port assembly 488 is typically relatively small. Nonetheless, the ability for this flow is highly desired in that the control port assembly 488 functions in combination with the RBC outlet port assembly 516 to automatically control the radial position of an interface between separated RBCs and the "buffy coat" in relation to the RBC dam 232 by controlling the radial position of an interface between separated RBCs and plasma in relation to the control port assembly 488. The control port assembly 488 and RBC outlet port assembly 516 automatically function to maintain the location of the interface between the separated RBCs and the buffy coat at a desired radial location within the channel 208 which is typically adjacent the RBC dam 232 such that there is no spillover of RBCs beyond the RBC dam 232. This function is provided by removing separated RBCs from the channel 208 at a rate which reduces the potential for RBCs and the other large cells as noted flowing beyond the RBC dam 232 and contaminating the platelet collection.

Separated platelets, which are disposed radially inwardly of the RBC layer and more specifically radially inwardly of the buffy coat, flow beyond the RBC dam 232 with the plasma (e.g., via platelet-rich plasma) in a clockwise direction. A generally funnel-shaped platelet collect well 236 is disposed in a clockwise direction from the RBC dam 232 and is used to remove platelets from the channel 208 in the platelet-rich plasma. The configuration of the platelet collect well 236 is defined by only part of the outer channel wall 216. The remainder of the platelet collect well 236 is defined by the blood processing vessel 352 when loaded in the channel 208.

The outer channel wall 216 is further configured to receive the platelet collect tube 424. Platelet collect tube recess 254 is disposed yet further radially outwardly from the platelet support recess 249 to provide this function. As such, the platelet collect tube 424 may extend radially outwardly from the outer sidewall 376 of the blood processing vessel 352, extend upwardly through the platelet collect tube recess 254 behind or radially outwardly from the support 428, and extend above the channel housing 204.

Platelet-poor plasma continues to flow in a clockwise direction through the channel 208 after the platelet collect well 236 and may be removed from the channel 208. In this regard, the channel 208 further includes a generally concave plasma outlet slot 256 which is disposed proximate the second end 288 of the channel 208 and intersects the channel 208 at its inner channel wall 212 in substantially perpendicular fashion. A plasma outlet port assembly 452 to the interior of the blood processing vessel 352 is disposed in this plasma outlet slot 256 such that plasma may be continually removed from the blood processing vessel 352 during an apheresis procedure (e.g., during continued rotation of the channel housing 204). This plasma may be collected and/or returned to the donor/patient 4. In order to increase the number of platelets that are separated and removed from the vessel 352 in a given apheresis procedure, the configuration of the channel 208 between the platelet collect well 236 and the plasma outlet slot 256 may be such that platelets which separate from plasma in this portion of the channel 208 actually flow in a counterclockwise direction back towards the platelet collect well 236 for removal from the channel 208. This may be provided be configuring the outer channel wall 216 such that it extends generally curvilinearly about the rotational axis 324 from the platelet collect well 236 to the plasma outlet slot 256 progressing generally inwardly toward the rotational axis 324 of the channel housing 204. Consequently, the portion of the channel 208 including the platelet collect well 236 and extending from the platelet collect well 236 to the second end 288 maybe referred to as a second stage 316 of the channel 208.

The channel 208 is also configured to provide platelet-poor plasma to the control port slot 264 and thus to the control port assembly 488 in order to assist in automatically controlling the interface between the RBCs and the buffy coat in relation to the RBC dam 232. In this regard, the first end 284 of the channel 208 is interconnected with the second end 288 of the channel 208 by a connector slot 260. With the first end 356 and second end 364 of the blood processing vessel 352 being fluidly joined, the connection therebetween may be disposed in this connector slot 260. As such, a continuous flowpath is provided within the blood processing vessel 352 and, for purposes of the automatic interface control feature, RBCs may flow to the control port slot 264 in a counterclockwise direction and plasma may flow to the control port slot 264 in a clockwise direction. The portion of the channel 208 extending from the first end 284 to the control port slot 264 may be referred to as a third stage 320 of the channel 208.

The configuration of the channel 208 retains the blood processing vessel 352 within the channel 208 throughout the apheresis procedure. This is particularly relevant in that the channel housing 204 is preferably rotated a relatively high rotational velocities, such as about 3,000 RPM.

Disposable Set: Blood Processing Vessel

As described, the blood processing vessel 352 is removably disposed within the channel 208 for directly interfacing with and receiving a flow of blood in an apheresis procedure. The use of the blood processing vessel 352 alleviates the need for sterilization of the channel housing 204 after each apheresis procedure and the vessel 352 may be discarded to provide a disposable system. Two preferable characteristics of the blood processing vessel 352 are that it is constructed such that it is sufficiently rigid to be free standing in the channel 208; however, it is also preferably sufficiently flexible so as to substantially conform to the shape of the channel 208 during an apheresis procedure.

The blood processing vessel 352 includes an inner sidewall 372 and an outer sidewall 376. In the illustrated embodiment, the blood processing vessel 352 is formed by sealing two pieces of material together (e.g., RF welding). More specifically, the inner sidewall 372 and outer sidewall 376 are connected along the entire length of the blood processing vessel 352 to define upper and lower seals. Seals are also provided on the ends of the vessel 352. By utilizing two separate sheets to form the blood processing vessel 352, a "flatter" profile may also be achieved. This type of profile is beneficial during rinseback, and also facilitates loading and unloading of the vessel 352 relative to the channel 208.

Centrifuge Rotor Assembly

The channel assembly 200 is mounted on the centrifuge rotor assembly 568 which rotates the channel assembly 200 to separate the blood into the various blood component types by centrifugation. A preferred centrifuge rotor assembly 568 is described in more detail in U.S. Pat. No. 5,722,946; inter alia.

Apheresis Protocol

One protocol which may be followed for performing an apheresis procedure on a donor/patient 4 utilizing the above-described system 2 will now be summarized. Initially, an operator loads the cassette assembly 110 onto the pump/valve/sensor assembly 1000 of the blood component separation device 6 and hangs the various bags (e.g., bags 114, 94, 84) on the blood component separation device 6. The operator then loads the blood processing vessel 352 into the channel 208 which is disposed on the channel housing 204 which is in turn mounted on the centrifuge rotor assembly 568.

With the extracorporeal tubing circuit 10 and the blood processing vessel 352 loaded in the above-described manner, the circuit 10 and vessel 352 are pressure tested to verify that there are no leaks. The donor/patient 4 is then fluidly interconnected with the extracorporeal tubing circuit 10 (by inserting an access needle 32 into the donor/patient 4). Moreover, the anticoagulant tubing 54 is primed between the anticoagulant supply (which interfaces with the spike drip member 52) and the manifold 28. Furthermore, blood return tubing 24 is primed by running the blood return peristaltic pump 1090 pump in reverse to draw priming solution through the blood return tubing 24, and into the reservoir 150 until solution is detected by the low level sensor 1320. The blood processing vessel 352 must then also be primed for the apheresis procedure.

When the blood processing vessel 352 contains blood and/or blood components throughout its entirety, the rotational velocity of the channel housing 204 is increased to its normal operation speed from about 2,750 RPM to about 3,250 RPM for a rotor diameter of about 10", and preferably about 3,000 RPM.

During the apheresis procedure, blood component types are separated from each other and removed from the blood processing vessel 352 on a blood component type basis. At all times during the apheresis procedure, the flow of whole blood is provided to the blood processing vessel 352 through the blood inlet port assembly 416 and is directed to the first stage 312. The control port dam 280 again reduces the potential for blood flowing in a counterclockwise direction in the channel 208.

In the first stage 312, blood is separated into a plurality of layers of blood component types including, from the radially outermost layer to the radially innermost layer, RBCs, WBCs, platelets, and plasma. As such, the RBCs sediment against the outer channel wall 216 in the first cell separation stage 312. By configuring the RBC dam 232 such that it is a section of the channel 210 which extends further inwardly toward the rotational axis 324 of the of the channel housing 204, this allows the RBC dam 232 to retain separated red blood cells in the first stage 312.

Separated RBCs are removed from the first stage 312 utilizing the above-noted configuration of the outer channel wall 216 which induces the RBCs to flow in a counterclockwise direction (e.g., generally opposite to the flow of blood through the first cell separation stage 312). That is, the portion of the channel 208 proximate the RBC outlet port assembly 516 is disposed further from the rotational axis 324 of the channel housing 204 than that portion of the channel 210 proximate the RBC dam 232. As such, separated RBCs flow through the first stage 312 in a counterclockwise direction along the outer channel wall 216, past blood inlet port assembly 388 on the blood processing vessel 352, and to an RBC outlet port assembly 516. Since the vertical slot 404 of the blood inlet port 392 is substantially parallel with the inner channel wall 212, the outer channel wall 216, the inner sidewall 372 of the blood processing vessel 352 and the outer sidewall 376 of the blood processing vessel 352, it directs the flow of blood in a clockwise direction in the channel 208 and thus toward the RBC dam 232. Since it is disposed proximate the inner channel wall 212, the introduction of blood into the blood processing vessel 352 does not substantially affect the flow of RBCs along the outer channel wall 216. Consequently, RBCs effectively flow undisturbed past the blood inlet port 392 and to the RBC outlet port assembly 516 for removal from the blood processing vessel 352. These RBCs may either be collected and/or provided back to the donor/patient 4.

Platelets are less dense then RBCs and are thus able to flow beyond the RBC dam 232 and to the platelet collect well 236 in platelet-rich plasma where they are removed from the blood processing vessel 352 by the platelet collect port assembly 416. Again, the blood processing vessel 352 via the support 428 and the outer channel wall 216 collectively define the platelet collect well 236 when the blood processing vessel 352 is pressurized.

Platelet-poor plasma is less dense than the platelets and continues to flow in a clockwise direction through the second stage 316 to the plasma outlet port assembly 452 where at least some of the plasma is removed from the blood processing vessel 352. This plasma may be collected and/or returned to the donor/patient 4. However, some of the plasma flow continues in the clockwise direction into and through the third stage 320 to the control port assembly 488 to provide for automatic control of the location of the interface between the RBCs and platelets in the above-described manner.

Platelet/RBC Collection

As noted, blood apheresis system 2 provides for contemporaneous separation of a plurality of blood components during blood processing, including the separation of red blood cells (RBCs), platelets and plasma. In turn, such separated blood components may be selectively collected in corresponding storage reservoirs or immediately returned to the donor/patient 4 during a blood return submode. In this regard, and in one approach where both platelets and RBCs are to be collected, blood apheresis system 2 may be advantageously employed to collect platelets, and if desired, separated plasma, during a time period(s) separate from the collection of red blood cells. In this manner, the collection of both high quality platelet units and high quality red blood cell units can be realized.

In this regard, the procedures described hereinabove are carried out to provide priming of extracorporeal tubing circuit 10 and blood processing vessel 352. The initiation of blood processing then provides for the collection of platelets in reservoir 84 during a first period and the collection of red blood cells in reservoir 954 during a second period. Plasma collection in reservoir 94 may also be selectively completed during the first period. During the platelet blood processing period and successive RBC collection procedure, blood component separation device 6 will control the initiation and termination of successive blood removal and blood return submodes, as described hereinabove. Additionally, blood component separation device 6 will control the platelet and RBC collection processes according to a predetermined protocol, including control over the divert valve assemblies 1100, 1110 and 1120 of the pump/valve/sensor assembly 1000.

More particularly, following priming, blood separation control device 6 provides control signals to pump/valve/sensor assembly 1000 so that platelet divert valve assembly 1100 diverts the flow of separated platelets pumped through platelet outlet tubing 66 and platelet tubing loop 142 into platelet collection tubing 82 for collection in reservoir 84. If plasma collection is desired, blood to component separation device 6 also provides control signals so that plasma divert valve assembly 1110 diverts the flow of separated plasma pumped through plasma outlet tubing 68 and plasma tubing loop 162 into plasma collector tubing 92 for collection in reservoir 94. Additionally, RBC/plasma divert valve assembly 1120 will continue to divert the flow of separated RBCs flowing through outlet tubing 64 through return tubing loop 172 and into blood return reservoir 150. When the desired volumes of platelets and plasma have been collected, blood component separation device 6 will selectively control divert assemblies 1100 and 1110 to divert the flow of platelets and plasma into reservoir 150.

Following completion of platelet and plasma collection, the RBC collection procedure is initiated via control signals provided by blood collection device 6. Such RBC collection procedure includes a setup phase and a collection phase. During the setup phase, the blood apheresis system 2 is adjusted to establish a predetermined hematocrit in those portions of the blood processing vessel 352 and extracorporeal tubing circuit 10 through which separated RBCs will pass for collection during the RBC collection phase.

More particularly, during the setup phase, and in order to realize a predetermined hematocrit of at least about 75%, a desired packing factor in the first stage 312 of the blood processing vessel 352 is established. Additionally, a desired AC ratio (i.e. the ratio between the inlet flow rate to vessel 352 (including whole blood plus anticoagulant AC) and the AC flow rate into tubing circuit 10) will be established. Further, the total uncollected plasma flow rate through blood processing vessel 352 and extracorporeal tubing circuit 10 will be established at a predetermined level. These adjustments are carried out in simultaneous fashion to establish the desired hematocrit in an expeditious manner. As will be appreciated, the adjusted AC ratio and predetermined hematocrit should be maintained during the subsequent RBC collection phase.

During the set-up phase, blood component separation device 6 provides appropriate control signals to the pump/valve/sensor assembly 1000 such that all separated blood components flowing out of processing vessel 352 will pass to return reservoir 150. Also, blood component separation device 6 will continue operation of blood inlet pump assembly 1030, including operation during each blood return submode.

In order to establish the desired packing factor, the operating speed of centrifuge rotor assembly 568 may be selectively established via control signals from blood component separation device 6, and the blood inlet flow rate to vessel 352 may be selectively controlled via control by blood component separation device 6 over pump assembly 1030. More particularly, increasing the rpms of centrifuge rotor assembly 568 and/or decreasing the inlet flow rate will tend to increase the packing factor, while decreasing the rpms and increasing the flow rate will tend to decrease the packing factor. As can be appreciated, the blood inlet flow rate to vessel 352 is effectively limited by the desired packing factor.

To establish the desired AC ratio, blood component separation device 6 provides appropriate control signals to anticoagulant peristaltic pump 1020 so as to introduce anticoagulant into the blood inlet flow at a predetermined rate, as previously described hereinabove. Relatedly, in this regard, it should be noted that the inlet flow rate of anticoagulated blood to blood processing vessel 352 is limited by a predetermined, maximum acceptable anticoagulant infusion rate (ACIR) to the donor/patient 4. As will be appreciated by those skilled in the art, the predetermined ACIR may be established on a donor/patient-specific basis (e.g. to account for the particular total blood volume of the donor/patient 4). To establish the desired total uncollected plasma flow rate out of blood processing vessel 352, blood collection device 6 provides appropriate control signals to plasma pump assembly 1060 and platelet pump assembly 1040. Relative to platelet collection, such control signals will typically serve to increase plasma flow through plasma outlet port 456, and thereby reduce plasma flow with RBCs through RBC outlet port 520. This serves to increase the hematocrit in the separated RBCs. Additionally, it is preferable for blood processing device 6 to provide control signals to platelet pump assembly 1040 so as to establish a predetermined flow rate wherein platelets and some plasma pass together through platelet port 420, thereby reducing platelet clumping downstream in tubing circuit 10. In this regard, such predetermined rate will be limited by the diameter of the platelet outlet tubing 66 and the size of the internal channels (e.g. 140a, 140b) within molded cassette 110.

In one embodiment, where centrifuge rotor assembly 568 defines a rotor diameter of about 10 inches, and where a blood processing vessel 352 is utilized, as described hereinabove, it has been determined that channel housing 204 can be typically driven at a rotational velocity of about 3000 rpms to achieve the desired hematocrit during the setup and blood collection phases. Correspondingly, the blood inlet flow rate to vessel 352 should be established at below about 64.7 ml/min. The desired hematocrit can be reliably stabilized by passing about two whole blood volumes of reservoir 352 through reservoir 352 before the RBC collection phase is initiated.

To initiate the RBC collection phase, blood component separation device 6 provides an appropriate control signal to RBC/plasma divert valve assembly 1120 so as to direct the flow of RBCs removed from blood processing vessel 352 into RBC collection reservoir 954. Both the platelet divert valve assembly 1100 and plasma divert valve assembly 1110 remain in a position to direct flow into reservoir 150 for return to donor/patient 4 during blood return submodes. In the later regard, it is preferable that, during blood return submodes of the RBC collection phase, blood collection device 6 provide appropriate control signals so as to stop the operation of all pump assemblies other than return pump assembly 1090. In this regard, stoppage of inlet pump assembly 1030 avoids recirculation of uncollected blood components into vessel 352 and resultant dilution of separated RBC components within vessel 352.

As will be appreciated, in the present invention separated RBCs are not pumped out of vessel 352 for collection, but instead are pushed out vessel 352 and through extracorporeal tubing circuit 10 by the pressure of the blood inlet flow to vessel 352. Consequently, trauma to the collected RBCs is minimized.

During the RBC collection phase, the inlet flow into vessel 352 is limited by the above-noted maximum, acceptable ACIR to the donor/patient 4. The desired inlet flow rate is also limited by that necessary to maintain the desired packing factor, as also discussed. In this regard, it will be appreciated that, relative to the setup phase, the inlet flow rate may be adjusted slightly upwards during the RBC collection phase since not all anticoagulant is being returned to the donor/patient 4. That is, a small portion of the AC remains with the plasma that is collected with the RBCs in RBC reservoir 954.

Following collection of the desired quantity of red blood cells, blood separation device 6 may provide a control signal to divert assembly 1120, so as to divert RBC flow to reservoir 150. Additionally, if further blood processing by apheresis is not desired, rinseback procedures may be completed. Additionally, the red blood cell reservoir 954 may be disconnected from the extracorporeal tubing circuit 10. A storage solution may then be added to the red blood cell reservoir or bag 954 preferably through the opening of optional frangible connector 968. Such storage solution may advantageously facilitate storage of the RBCs for up to about 42 days at a temperature of about 1–6 C.

While one approach for platelet and RBC collection has been described above, other approaches will be apparent. By way of primary example, the described RBC collection procedure may be carried out following blood priming, and prior to platelet collection. Such an approach would advantageously allow RBC collection to occur in the course of AC ramping, thereby reducing total processing time requirements. That is, since AC ramping up to a predetermined level is typically, gradually completed prior to the start of a platelet collection procedure (e.g. so as to maintain an acceptable ACIR), completing PBC collection procedures in the course of AC ramping would reduce the overall processing time for RBC and platelet collection.

Further, and as noted above, plasma collection could occur contemporaneous with RBC collection. Additionally, in this regard, plasma collection could occur during both platelet and RBC collection procedures, depending upon the volume of plasma product desired. Finally, it has been recognized that the present invention may also be employable to simultaneously separate and collect both red blood cells and platelets, and if desired, plasma.

Graphical Computer Interface

In order to assist an operator in performing the various steps of the protocol being used in an apheresis procedure with the apheresis system 2, the apheresis system 2 further preferably includes a computer graphical interface 660 as illustrated in FIG. 1. The following description describes an interface for use by an English language speaking operator. For other operations and/or languages, the textual portions of the interface would, of course, be adapted accordingly. The graphical interface 660 includes a computer display 664 which has "touch screen" capabilities. Other appropriate input devices (e.g., keyboard) may also be utilized alone or in combination the touch screen. For example, a pump pause and a centrifuge stop button of the well known membrane type may be provided. The graphics interface 660 not only allows the operator to provide the necessary input to the apheresis system 2 such that the parameters associated with operation of the apheresis system may be determined (e.g., data entry to allow determination of various control parameters associated with the operation of the apheresis system 2), but the interface 660 may also assist the operator by providing pictorials of certain steps of the apheresis procedure. Moreover, the interface 660 may also effectively convey the status of the apheresis procedure to the operator. Furthermore, the interface 660 also may be used to activate standardized corrective actions (i.e., such that the operator need only identify the problem and indicate the same to the interface 660 which will then direct the apheresis system 2 to correct the same). Descriptions and procedures for various of these features as presently preferred in utilizing an interface like interface 660 may be found in U.S. Pat. Nos. 5,653,887 and 5,941,842; inter alia.

Figure 7:
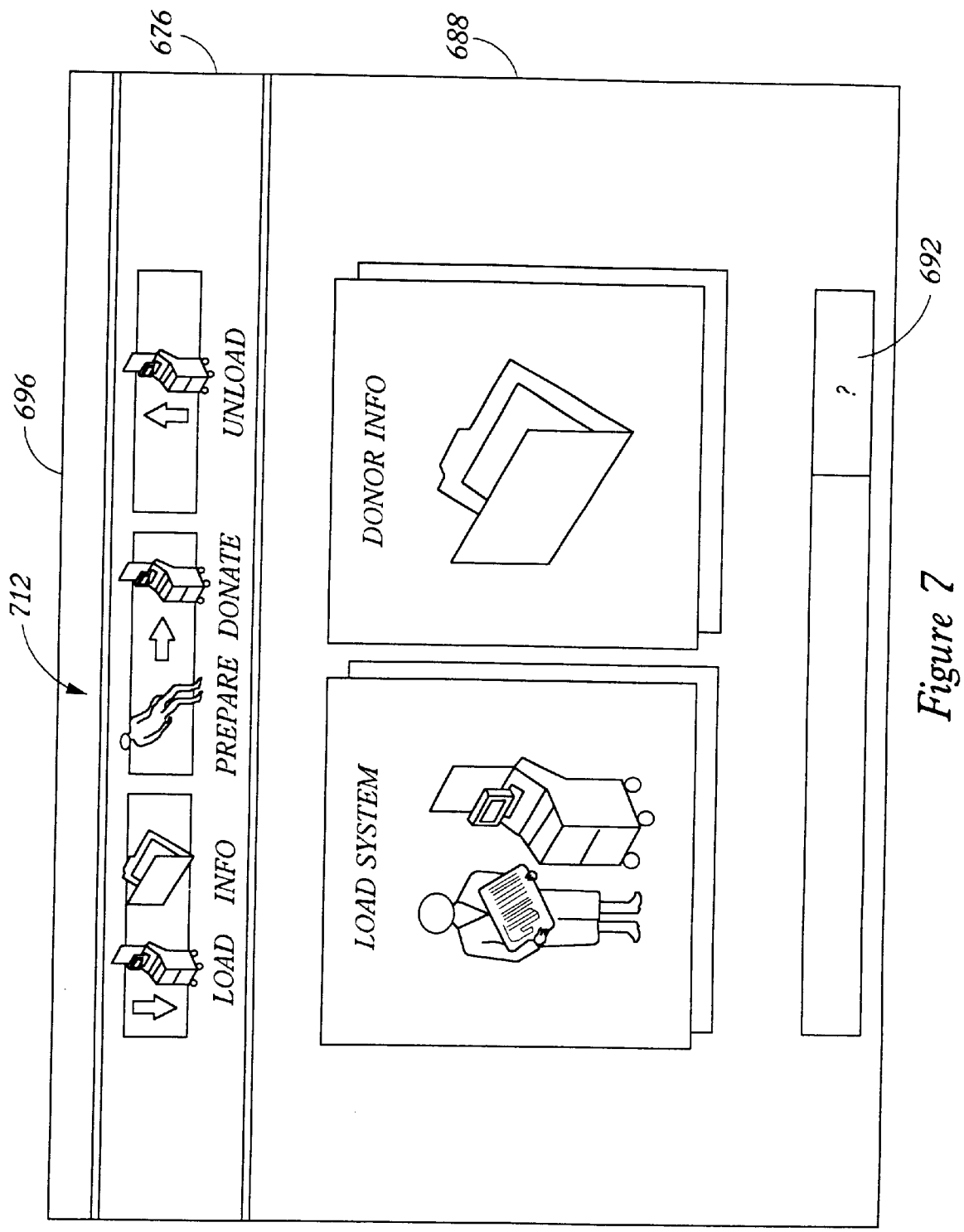
FIG. 7 is a "master screen" for the computer graphics interface of the apheresis system of FIG. 1.

Even so, some alternative applications of an interface such as interface 660 with the alternative embodiments of the present invention will now be described. These applications may likely be considered relative to the corrective actions described briefly above. In particular, and first referring to FIG. 7, at the start of an apheresis procedure a master screen 696 is displayed to the operator on the display 664. The master screen 696, as well as each of the screens displayed to the operator by the interface 600, includes a status bar 676. The status bar 676 preferably includes various icons representing various steps in the overall apheresis procedure as described in more detail in the above-referenced U.S. patents. The status bar 676 preferably also includes a status line area 712. Such a status line area 712 provides for textually conveying status messages to the operator concerning certain phases of the operation of the blood component separation device 6.

The master screen 696, as well all other screens displayed to the operator by the interface 660 during an apheresis procedure, also include a work area 688. The work area 688 provides multiple functions. Initially, the work area 688 displays additional information (pictorially and textually in some instances) on performing the apheresis procedure to the operator (e.g., certain additional substeps of the apheresis procedure, and/or addressing certain "conditions" encountered during the apheresis procedure). Moreover, the work area 688 also displays additional information on the status of the apheresis procedure to the operator. Furthermore, the work area 688 also provides for operator interaction with the computer interface 660, such as by allowing/requiring the operator to input certain information. Touch screen capabilities are preferable here.

In the event that the operator requires additional guidance with regard to any of the steps presented on a procedure or status screen, the operator may touch the help button 692 which may be provided on any screen. This may then display a menu of screens (not shown) which the operator may view and/or may sequentially present a number of help screens (not shown) associated with the particular screen. Moreover, the help screen may provide the operator with more detail, in the nature of additional pictorials and/or text, regarding one or more aspects of the particular procedure or operational status of interest. Various of the included screens in the graphics interface 660 may include a help button 692 to provide this help feature.

Figure 8:
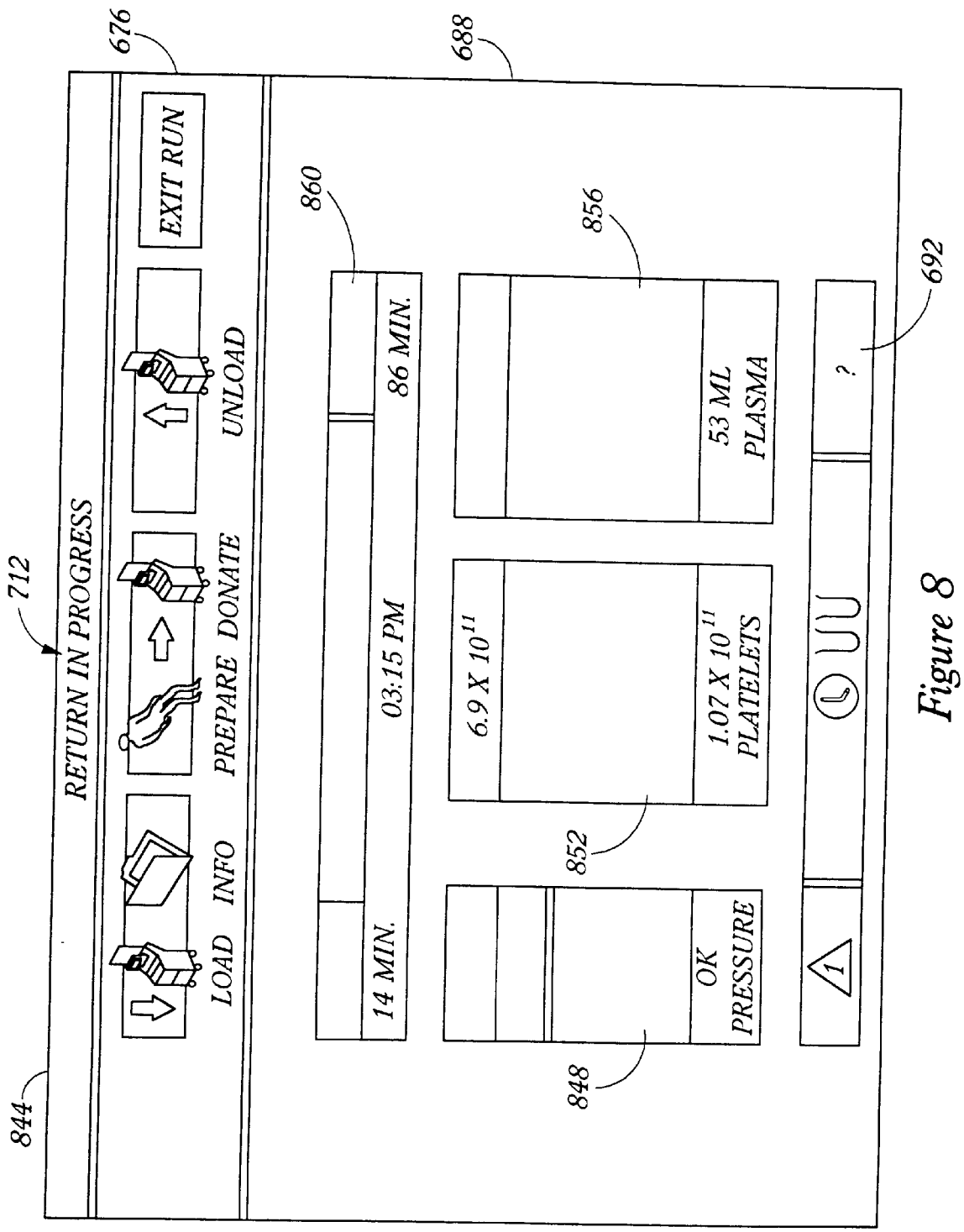
FIG. 8 is a "run screen" for the computer graphics interface of the apheresis system of FIG. 1.

Once the operator completes all of the donor/patient prep steps and has fully initiated the blood flow and separation procedure (as may be aided by a series of screens not shown here; see the above-referenced U.S. patents), a run screen such as the screen 844 illustrated in FIG. 8 may be displayed. The run screen 844 may primarily display information to the operator regarding the apheresis procedure. For example, the run screen 844 shown in FIG. 8 includes a blood pressure display 848 (i.e., to convey to the operator the donor/patient's extracorporeal blood pressure), a platelet collect display 852 (i.e., to convey to the operator an estimate of the number of platelets which have been currently collected), a plasma collect display 856 (i.e., to convey to the operator the amount of plasma which has been currently collected), and a time display 860 (e.g., both the amount of time which has lapsed since the start of the collection procedure (the left bar graph and noted time), as well as the amount of time remaining in the collection procedure (the right bar graph and noted time). A control button (not shown) may be provided to toggle between the time remaining display and the start and stop time display.

The run screen 844 may also display, in the case of a single needle procedure (i.e., where only one needle is utilized to fluidly interconnect the donor/patient 4 with the blood component separation device 6), whether blood is being withdrawn from the donor/patient 4 (e.g., by displaying text such as "draw in progress" in the status line area 712) or is being returned to the donor/patient 4 (e.g., by displaying the textual phrase "return in progress" as shown in the status line area 712 in FIG. 8). This information may be useful to the donor/patient 4 in that if the donor/patient 4 is attempting to maintain a certain blood pressure by squeezing an article to assist in removal of blood from the donor/patient 4, the donor/patient 4 will be provided with an indication to suspend these actions while blood is being returned to the donor/patient 4.

Figure 9:
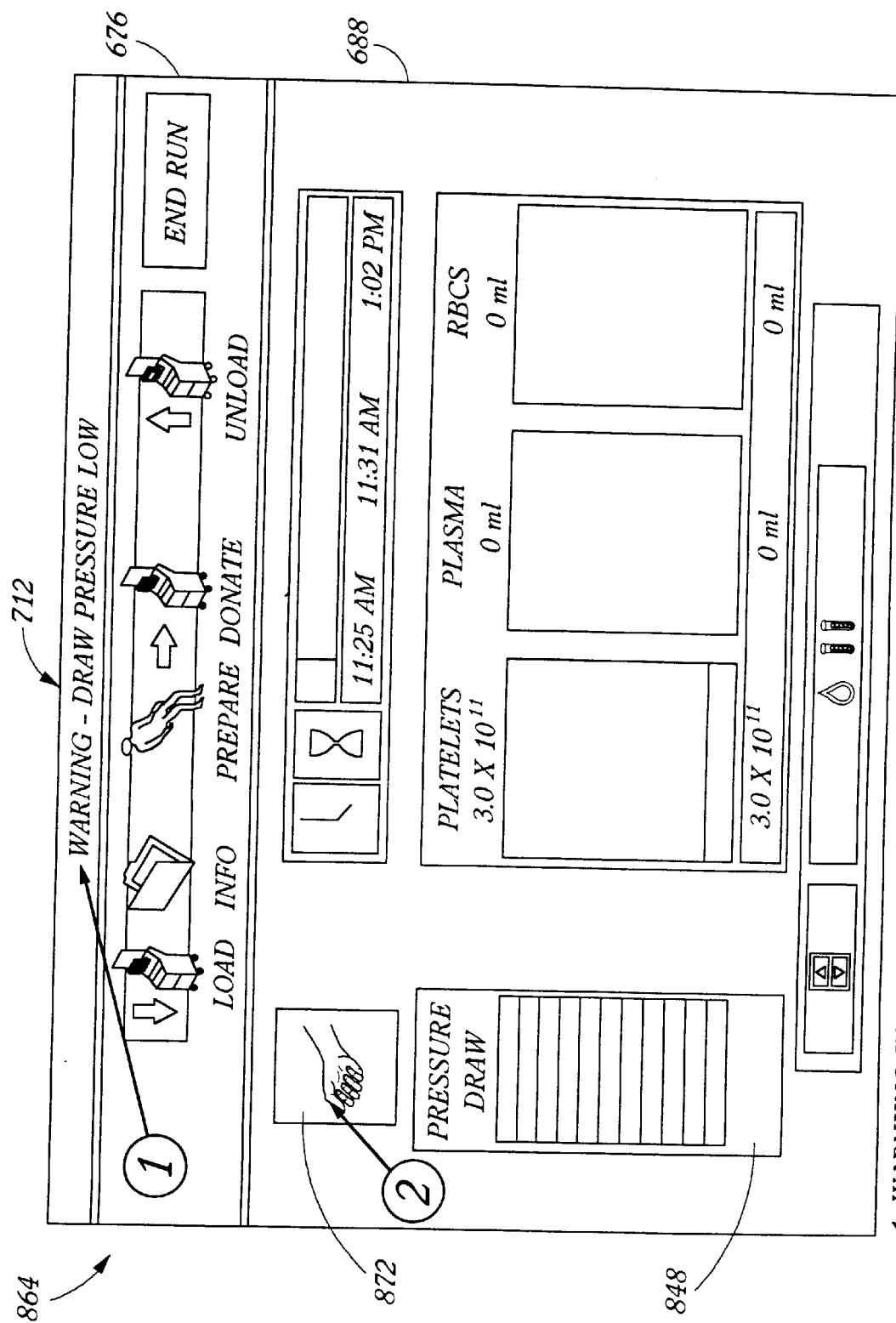
FIG. 9 is one embodiment of an "warning screen" for the computer graphics interface of the apheresis system of FIG. 1; and, FIG. 10 is a "alarm screen" for the warning screen of FIG. 9.

During the apheresis procedure, certain conditions may be detected by the apheresis system 2 which would benefit from intervention and/or investigation by the donor/patient or the operator. If one of these types of conditions is detected, appropriate warning and/or alarm screens may be displayed to the operator. One embodiment of a warning screen 864 is illustrated in FIG. 9. Initially, the warning screen 864 textually conveys a potential problem with the system 2 via the textual message displayed in the status line area 712. As shown in FIG. 9, the warning depicted in the presently displayed embodiment is that the draw pressure is too low. This warning would be indicated when the pressure level has been reached as calculated or set in whichever alternative embodiment is being used as described above. The text may be useful in ensuring that the operator understands the problem. Other warning sounds or flashing lights may also be emitted and/or displayed by the separation device 6 whether as a part of the display screen 660 or separately. The warning screen 864 also preferably includes an action pictorial 872 which graphically conveys to the operator the action which should be taken in relation to the problem. These are actions which may be difficult or impossible for the system 2 to take itself. In the present example, a squeeze icon is displayed to convey that the donor/patient should squeeze his or her fist in order to raise the access/draw pressure.

Figure 10:
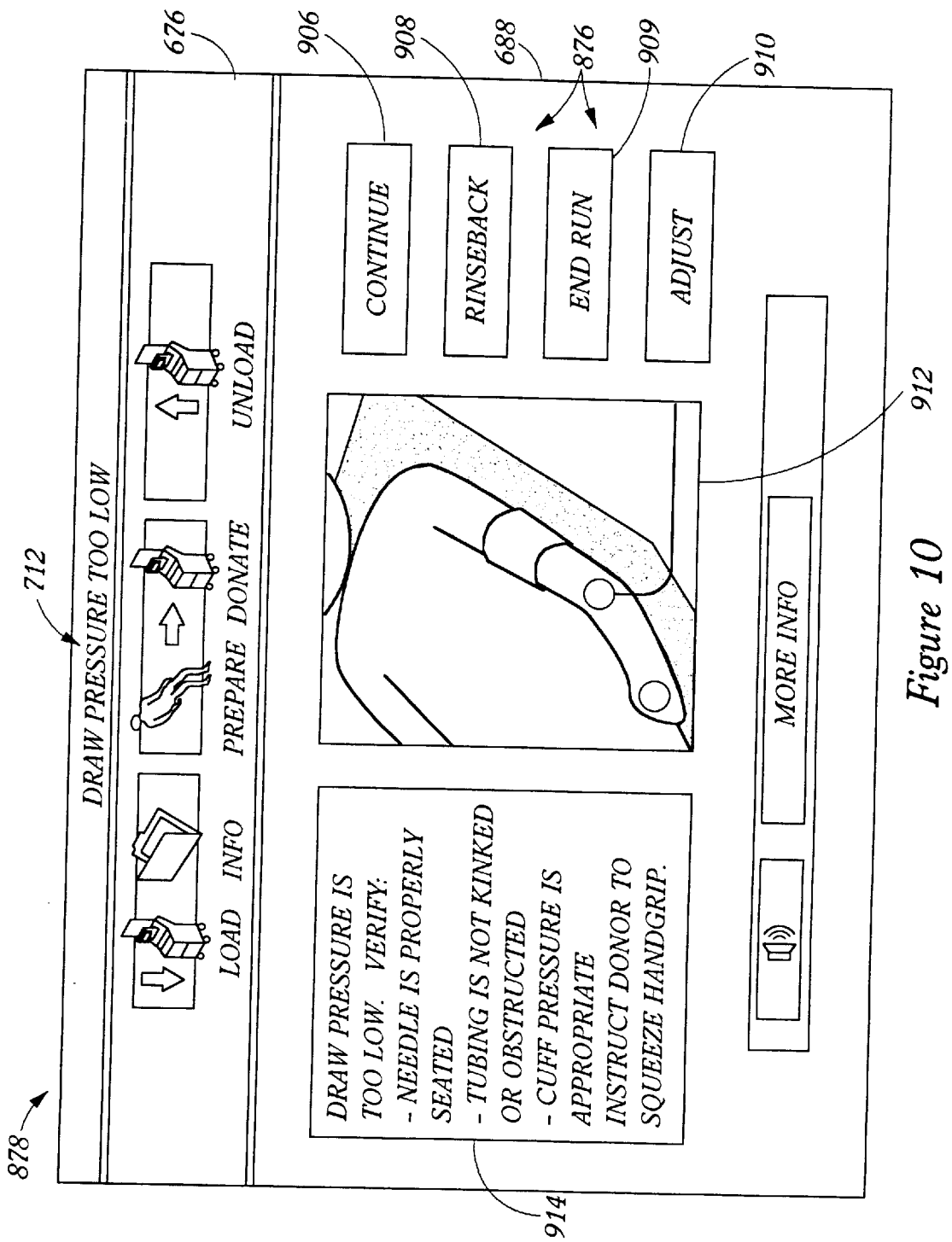

If the access/draw pressure does not resolve (by any of the pre-selected methods as described above), then a regular/full alarm may be indicated as shown by the screen 878 in FIG. 10. In FIG. 10, a textual message "draw pressure too low" is displayed in the textual line area 712, and further text (in area 914) is displayed in the work area 688 representing various alternative system elements and/or functions which should be inspected by the operator to ensure proper system operation. A pictorial representation 912 of the system elements and/or functions is also displayed in the work area 688. Finally, the alarm screen 878 preferably includes an inspection results array 876 which allows the operator to indicate the results or a desired next operational procedure as a result of the inspection. In the illustrated embodiment, the array 876 includes a continue button 906, a rinseback button 908, an end run button 909 and an adjust button 910. These are preferably touch activated buttons for use on a touch sensitive screen 664.

Depending upon the selection made by the operator on the inspection results array 876, additional questions may be posed to the operator in further screens which require further investigation and/or which specify the desired remedial action. For example, the adjust button 910 can take the operator to another screen (not shown) to adjust the flow rate or rates for this particular donor/patient. The alarm screen 878 includes a remedial action pictorial 912 and remedial action text 914 to convey to the operator how to correct the identified problem.

The computer interface 660 may also allow the operator to initiate some type of corrective action based upon observations made by and/or conveyed to the operator. For instance, various screens of the interface 660 may include a trouble shooting button (not shown), a preferred embodiment of which is described in the above-referenced U.S. patents. Flow rate adjustments may also (alternatively and/or additionally) be made available through trouble shooting buttons such as these.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A method for controlling a fluid separation system in response to fluid pressure changes in a fluid flow, said method comprising the steps of:

sensing a fluid pressure value;

comparing the fluid pressure value to a threshold value, and if there is an occurrence where the fluid pressure value is below the threshold value, then pausing fluid flow; and resuming fluid flow when the fluid pressure value being sensed rises above a discrete set point.

2. A method according to claim 1 in which the discrete set point is −50 mmHg.

3. A method according to claim 1 in which the method further comprises the step of:

emitting a warning alarm signal contemporaneously with said step for pausing fluid flow.

4. A method according to claim 3 in which said warning alarm signal is an audible squeeze beep sound.

5. A method for controlling a fluid separation system in response to fluid pressure changes in a fluid flow, said method comprising the steps of:

sensing a fluid pressure value;

comparing the fluid pressure value to a threshold value, and if there is an occurrence where the fluid pressure value is below the threshold value, then pausing fluid flow; and setting a full alarm condition when the fluid pressure value sensed does not automatically resolve to above a discrete set point within a selected period.

6. A method according to claim 5 in which said step of setting a full alarm condition occurs after the expiration of the selected period.

7. A method according to claim 5 in which the method further comprises the step of:

interpreting a particular quantity of occurrences of fluid pressure values below the threshold value within a particular time period, and then, signaling a full alarm condition.

8. A method according to claim 7 in which the particular quantity of occurrences of fluid pressure values below the threshold value is set to be three.

9. A method according to claim 7 in which the particular time period is three minutes.

10. A method for controlling a fluid separation system in response to fluid pressure changes in a fluid flow, said method comprising the steps of:

sensing a fluid pressure value;

comparing the fluid pressure value to a threshold value, and if there is an occurrence where the fluid pressure value is below the threshold value, then pausing fluid flow for a selected period;

and whereby the threshold value is established in view of certain pre-selected flow parameters including flow rate and fluid viscosity.

11. A method according to claim 10 in which the fluid separation system has an inlet tubing for fluid flow, and a needle for fluid flow into the inlet tubing, such that the threshold value is:

$$\text{Threshold Value} = \text{Config} + 75 - 0.3309 * Q_{in}/(1-H_{in}) - 0.3026 * Q_n/(1-H_n);$$

where,
Config=a configuration pre-selected pressure value;
$Q_{in}$=fluid flow rate in the inlet tubing line;
$H_{in}$=fluid Hematocrit in the inlet tubing line;
$Q_n$=fluid flow rate in the needle; and
$H_n$=fluid Hematocrit in the needle.

12. A method according to claim 10 in which the fluid separation system has an inlet tubing for fluid flow, and a needle for fluid flow into the inlet tubing; such that the threshold value is:

Threshold Value=Config+75−0.3309*$Q_{in}$/(1−$H_{in}$)−0.5602*$Q_n$/(1−$H_n$);

where,
Config=a configuration pre-selected pressure value;
$Q_{in}$=fluid flow rate in the inlet tubing line;
$H_{in}$=fluid Hematocrit in the inlet tubing line;
$Q_n$=fluid flow rate in the needle; and
$H_n$=fluid Hematocrit in the needle.

13. A method according to claim 10 in which the fluid separation system has a return tubing for fluid flow, and a needle for fluid flow from the return tubing; such that the threshold value is:

Threshold Value=Config−50−0.3309*$Q_{in}$/(1−$H_{in}$)−0.3026*$Q_n$/(1−$H_n$);

where,
Config=a configuration pre-selected pressure value;
$Q_{in}$=fluid flow rate in the return tubing line;
$H_{in}$=fluid Hematocrit in the return tubing line;
$Q_n$=fluid flow rate in the needle; and
$H_n$=fluid Hematocrit in the needle.

14. A method according to claim 10 in which the fluid separation system has a return tubing for fluid flow, and a needle for fluid flow from the return tubing; such that the threshold value is:

Threshold Value=Config−50−0.3309*$Q_{in}$/(1−$H_{in}$)−0.5602*$Q_n$/(1−$H_n$);

where,
Config=a configuration pre-selected pressure value;
$Q_{in}$=fluid flow rate in the return tubing line;
$H_{in}$=fluid Hematocrit in the return tubing line;
$Q_n$=fluid flow rate in the needle; and
$H_n$=fluid Hematocrit in the needle.

15. A fluid separation control system which includes:
a fluid pressure monitoring device;
at least one fluid flow control assembly; and
a process control device which is in signal receiving communication with the fluid pressure monitoring device and signal sending communication with the at least one fluid flow control assembly;
whereby said fluid pressure monitoring device measures a fluid pressure value and communicates a signal to said process control device representative of the fluid pressure value measured thereby, and whereby said process control device interprets the signal received thereby from said pressure monitoring device and if the pressure indicated thereby is below a threshold value, the process control device sends a warning alarm signal to said fluid flow control assembly to pause fluid flow for a period until the fluid pressure measured by the pressure monitoring device automatically resolves above a discrete set point.

16. A control system according to claim 15 in which a full alarm condition is initiated after fluid flow has been paused for a selected period.

17. A control system according to claim 15 in which a warning alarm signal is caused to be emitted by the control system.

18. A control system according to claim 17 in which said warning alarm signal is an audible squeeze beep sound.

19. A control system according to claim 15 in which the control device interprets a particular quantity of warning alarm signals occurring within a particular time period as a trigger for setting a full alarm condition.

20. A control system according to claim 19 in which the particular quantity of warning alarm signals is pre-set at three.

21. A control system according to claim 19 in which the particular time period is pre-set at three minutes.

22. A control system according to claim 15 whereby the threshold value is established in view of certain pre-selected flow parameters including flow rate and fluid viscosity.

23. A control system according to claim 22 in which the fluid separation system has an inlet tubing for fluid flow, and a needle for fluid flow into the inlet tubing; such that the threshold value is:

Threshold Value=Config+75−0.3309*$Q_{in}$/(1−$H_{in}$)−0.3026*$Q_n$/(1−$H_n$);

where,
Config=a configuration pre-selected pressure value;
$Q_{in}$=fluid flow rate in the inlet tubing line;
$H_{in}$=fluid Hematocrit in the inlet tubing line;
$Q_n$=fluid flow rate in the needle; and
$H_n$=fluid Hematocrit in the needle.

24. A control system according to claim 22 in which the fluid separation system has an inlet tubing for fluid flow, and a needle for fluid flow into the inlet tubing; such that the threshold value is:

Threshold Value=Config+75−0.3309*$Q_{in}$/(1−$H_{in}$)−0.5602*$Q_n$/(1−$H_n$);

where,
Config=a configuration pre-selected pressure value;
$Q_{in}$=fluid flow rate in the inlet tubing line;
$H_{in}$=fluid Hematocrit in the inlet tubing line;
$Q_n$=fluid flow rate in the needle; and
$H_n$=fluid Hematocrit in the needle.

25. A control system according to claim 22 in which the fluid separation system has a return tubing for fluid flow, and a needle for fluid flow from the return tubing; such that the threshold value is:

Threshold Value=Config−50−0.3309*$Q_{in}$/(1−$H_{in}$)−0.3026*$Q_n$/(1−$H_n$);

where,
Config=a configuration pre-selected pressure value;
$Q_{in}$=fluid flow rate in the return tubing line;
$H_{in}$=fluid Hematocrit in the return tubing line;
$Q_n$=fluid flow rate in the needle; and
$H_n$=fluid Hematocrit in the needle.

26. A control system according to claim 22 in which the fluid separation system has a return tubing for fluid flow, and a needle for fluid flow from the return tubing; such that the threshold value is:

Threshold Value=Config−50−0.3309*$Q_{in}$/(1−$H_{in}$)−0.5602*$Q_n$/(1−$H_n$);

where,
Config=a configuration pre-selected pressure value;
$Q_{in}$=fluid flow rate in the return tubing line;
$H_{in}$=fluid Hematocrit in the return tubing line;
$Q_n$=fluid flow rate in the needle; and
$H_n$=fluid Hematocrit in the needle.

27. A method for pressure control in a single needle fluid separation system in which separated fluid components are first accumulated in a reservoir, and the accumulated fluid components are then cyclically pumped out of the reservoir, said method comprising the steps of:

sensing a fluid pressure value;

comparing the fluid pressure value to a threshold value, and if the fluid pressure value is below the threshold value, then pausing fluid flow for a selected period;

and simultaneously with the pausing step, pumping the accumulated fluid components out of the reservoir.

28. A method according to claim 27 in which the fluid is blood drawn from a donor/patient and the accumulated fluid components in the reservoir are blood components to be pumped back to the donor/patient.

29. A method according to claim 28 in which the blood is alternately drawn and returned in a repeating cycle, and in which the method step of pumping the accumulated fluid components out of the reservoir is conditioned upon the accumulation of fluid components being greater than a pre-selected percentage of completion.

30. A method according to claim 29 in which the percentage of completion is set at 90%.

31. A method for pressure control in a fluid separation system in which an unseparated source fluid is pumped into a separation vessel and two or more separated fluid components are removed from the separation vessel, at least a first one of the separated fluid components being pumped from the separation vessel and flowed through a fluid chamber for further separation, said method comprising the steps of:

sensing a fluid pressure value of the unseparated source fluid;

comparing the sensed fluid pressure value to a threshold value, and if the sensed fluid pressure value is below the threshold value, then pausing fluid flow of the unseparated source fluid for a selected period.

32. A method according to claim 31 further comprising the step of continuously pumping the first one of the separated fluid components from the separation vessel and continuously flowing it through the fluid chamber simultaneously with the pausing step for the selected period.

33. A method according to claim 31 in which the first one of the separated fluid components comprises platelets and the fluid chamber traps white blood cells therein.

* * * * *